(12) United States Patent
Fromm et al.

(10) Patent No.: US 9,758,545 B2
(45) Date of Patent: Sep. 12, 2017

(54) SENSOR WITH A SCAFFOLD HAVING CHANGEABLE CONFORMATIONS

(75) Inventors: Katharina Fromm, Fribourg (CH); Christian Bochet, Chavannes-de-Bogis (CH)

(73) Assignee: UNIVERSITÉ DE FRIBOURG (CH)

( * ) Notice: Subject to any disclaimer, the term of this patent is extended or adjusted under 35 U.S.C. 154(b) by 407 days.

(21) Appl. No.: 13/880,844

(22) PCT Filed: Oct. 24, 2011

(86) PCT No.: PCT/EP2011/068563
§ 371 (c)(1),
(2), (4) Date: Jun. 24, 2013

(87) PCT Pub. No.: WO2012/052566
PCT Pub. Date: Apr. 26, 2012

(65) Prior Publication Data
US 2013/0266644 A1    Oct. 10, 2013

(30) Foreign Application Priority Data

Oct. 22, 2010    (EP) ..................................... 10188556

(51) Int. Cl.
*C07H 21/04* (2006.01)
*C12Q 1/04* (2006.01)
*G01N 33/543* (2006.01)

(52) U.S. Cl.
CPC ............... *C07H 21/04* (2013.01); *C12Q 1/04* (2013.01); *G01N 33/54373* (2013.01)

(58) Field of Classification Search
CPC ..... C12Q 1/04; C07H 21/04; G01N 33/54373
See application file for complete search history.

(56) References Cited

U.S. PATENT DOCUMENTS

2003/0171711 A1    9/2003    Rohr et al.

FOREIGN PATENT DOCUMENTS

WO    WO 2005/098049 A2    10/2005

OTHER PUBLICATIONS

Stevanoic et al., Current Nanoscience, 2009, 5, 00-00.*
Song Jie et al., "Functional Self-Assembling Bolaamphiphilic Polydiacetylenes as Colorimetric Sensor Scaffolds", Journal of the American Chemical Society, vol. 126, No. 27, Jul. 14, 2004, pp. 8459-8465.
Ju Young Min et al., "A dexamethasone-loaded PLGA micirospheres/collagen scaffold composite for implantable glucose sensors", Journal of Biomedical Materials Research, vol. 93A, No. 1, Apr. 2010, pp. 200-210.
Gordon Oliver et al., "Silver Coordination Polymers for Prevention of Implant Infection: Thiol Interaction, Impact on Respiratory Chain Enzymes, and Hydroxyl Radical Induction", Antimicrobial Agents and Chemotherapy, vol. 54, No. 10, Oct. 2010, pp. 4208-4218.
International Search Report dated Nov. 11, 2011 for Int'l Appl. No. PCT/EP2011/068563.

* cited by examiner

*Primary Examiner* — Robert Cabral
(74) *Attorney, Agent, or Firm* — Stephen M. Lund

(57) ABSTRACT

The present invention relates to a scaffolded sensor with a container comprising a drug for triggering drug release, wherein the scaffold is intrinsically conformationally metastable and a method to its manufacture.

8 Claims, 8 Drawing Sheets

SENSOR WITH A SCAFFOLD HAVING CHANGEABLE CONFORMATIONS

CROSS-REFERENCE TO RELATED APPLICATIONS

Figure 1:
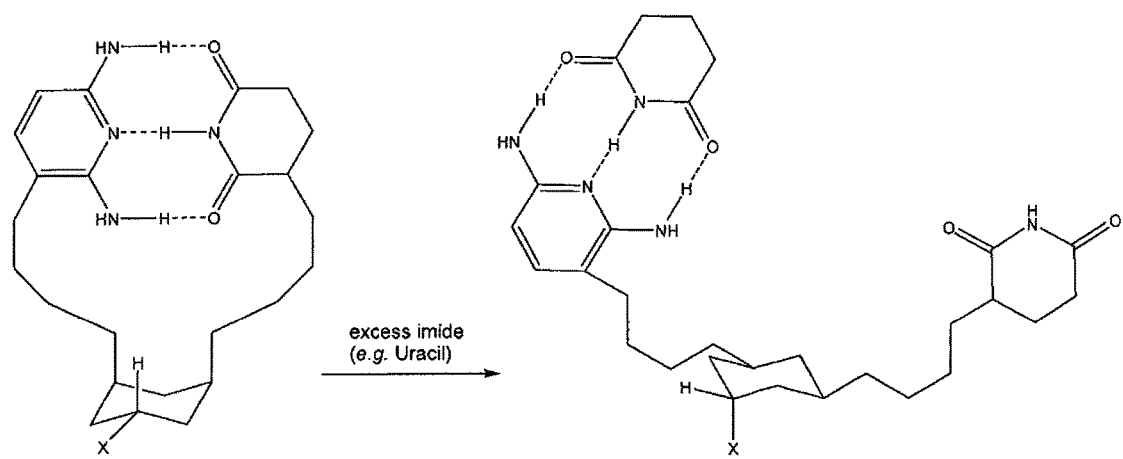

This application is a U.S. National Stage application, claiming benefit under 35 U.S.C. §§120 and 365 of International Application No. PCT/EP2011/068563, filed Oct. 24, 2011, and claiming benefit under 35 U.S.C. §119 of European Application No. 10188556.4, filed Oct. 22, 2010, the entire disclosures of both prior applications being incorporated herein by reference in their entirety.

FIELD OF THE INVENTION

The present invention relates to a scaffolded sensor, in particular to a scaffolded bacterial sensor, to prevent bacterial infections or detect bacteria in solutions.

Due to an increasing number of patients requiring joint replacements or internal fixations, preventing inflammation of the implant is of high importance. The replacements of knees, hips or shoulders are quite common, while even more prostheses and fracture fixations are applied.

Thereby is one of the problems that joint replacements and fracture fixation devices always bear the risk of infections which can become a very serious problem. But not only joints are replaced, but also organs, bones, blood vessels and other tissue replacements. Although advances in implant materials (short term or permanent) are achieved, as well as operation techniques allow more and more implant operations to be carried out, at the same time the risk of an infection increases.

DESCRIPTION OF THE INVENTION

The infection rate for knee implants lies in the range of 1-2% in contrast to 20% for implantations of pacemakers. These infections occur frequently perioperatively by bacterial contamination of the surgical site. In general, an early infection is caused by the bacteria *S. aureus*, if delayed mostly low virulence organisms including *S. epidermidis*, are responsible. Bacteria in implants typically proliferate and cluster in multilayers of exopolysaccharides, widely known as so-called biofilms.

These biofilms allow bacteria to resist antimicrobial agents and immune reactions of the body. Therefore it is impossible to treat them with "normal" antibiotics. Leading to dramatic complications for the patient or death in the worst case and to higher infection rates in the future, also accompanied with high costs for the health system.

Therefore, due to the health risk, as well as the increasing costs for medical treatment in such cases, prevention of early infection is a major clinical concern.

The formation of these biofilms and adhesions are well-developed survival strategies for bacteria in natural environments and also on the surface of implants. Biofilms can lead to inflammatory host responses, due bacterial multiplication (septic failure) or aseptic failures caused by bacterial components (polysaccharides) and microparticles of bacterial or material debris.

In the state of the art, the protection of infections by pharmaceuticals at the material surface is known, which entails the entrapment and immobilization of packaged substances and their subsequent leaching under steady release.

Therefore coatings were developed, releasing constantly antimicrobial drugs, which assure either good repulsion of bacterial adhesion on the implant and provide good tissue-integration or osseointegration. So far, no coating could provide both at the same time. However, the U.S. Pat. No. 7,455,911 discloses an anti-adhesive coating to prevent bacterial adhesion, but inhibits cell adhesion.

Other approaches were made, such as surface-treatments with hydrophilics to reduce the number of adhering organisms and their specific adhesion strength. Alternatively, nano-structured surfaces were provided, which enabled osteoinduction, but had no influence on bacteria at all.

The attempt to provide antibacterial surfaces was achieved by attaching antibiotics covalently to metal surfaces, e.g. in catheters, but this led only to a short-term elimination of *Staphylococcus* (*S.*) *aureus* and other bacteria.

Another successful approach was made by integrating antibiotics into implant cements. But only 30% of the applied antibiotics was available, as the remaining parts were either decomposed by temperature (e.g. Vancomycin is temperature sensitive above 25° C., and lacks long-term stability) or remained covalently bound in the implant.

The release of the drug was enabled by application of porous titanium foams, but all these attempts could not solve the problem that bacteria do get resistant to antibiotics with time. The continuous increase in bacterial resistance to antibiotics worldwide is currently observed, rendering the battle against infections more and more difficult. Resistance to lactam antibiotics is a major problem in hospitals, methicillin-resistant *S. aureus* (MRSA) and *Staphylococcus* (*S.*) *epidermidis* (MRSE) infections being predominant in systemic and implant-associated infections respectively. Coagulase-negative staphylococci (e.g. *S. epidermidis*) are the most common organism introduced during implantation, since they directly adhere to foreign body materials, while *S. aureus* is a typical organism, which colonizes implants after implantation, as it adheres to foreign surfaces covered with host proteins.

To provide long-term stable drugs in the battle against bacterial resistance, the application of silver ions was rediscovered. The effect on bacteria is non-specific, due to interferences with various enzymes, e.g. enabling the synthesis of the bacterial cell wall. Although the scientific world fears a bacterial resistance as for antibiotics it seems not possible for silver application. But due to their non-specificity, silver ions could also do harm on essential bacteria, e.g. in the flora of intestine such as bacteria, archaea or eukaryote.

Therefore not only drug release from surfaces was investigated, but also the use of nano-structured containers for drug delivery by diffusion and/or dilution mechanisms. Such systems have been focused mainly on the treatment of neurodegenerative diseases, such as epilepsy or cancer tumors. Among the known container systems, polymer-based vesicles as well as oxidic materials have been studied in order to obtain hollow nanospheres. Various nanospheres were tested for drug delivery made from Au, CuS or AlO(OH). Furthermore, oxidic systems such as $CeO_2$, $SnO_2$, $SiO_2$—CaO, or $TiO_2$ were successfully tested for their biocompatibility, but beside good bio-qualities the introduction of antibacterial compounds presents a difficult task which cannot be solved by the known methods.

Therefore, oxide materials precursors, based on polymer networks, have been studied to provide nanospheres containing silver ions with good stability and solubility. But although the silver ions show good results, the unsolved problem is still controlling the release of the drugs of nanospheres.

Attached to different metallic surfaces (Au, Ti), antibacterial effects were successful tested in medical applications. Additionally, different methods for antibacterial surface coatings were investigated. Disadvantageous is, that the coating shows antibacterial qualities, but no sensitiveness whether bacteria are actually present or not. Therefore bacteria resistance is also for coatings a big problem.

To prevent bacterial resistance a sensor for bacteria could initiate selective drug release. Although providing systems to detect and classify bacteria is difficult due to the large variety of bacteria and their differing metabolism, this was successful within in vitro tests, with multi-array electrochemical sensors or microcalorimetry via detection of oxygen consumption. Disadvantageously, there exist not only oxygen consuming bacteria but also anaerobic bacteria e.g. rot-causing bacteria like *P. vulgaris, P. pyocynea, G. lamblia* which are not detectable by this method.

Another starting point is the identification of the presence of bacteria involving quorum-sensing or extracellular plasmids and RNA. In the context of DNA sensing, recognition reactions have been established which might be useful in the context of bacterial genome sensing. In detail, DNA-chips have been found to be selective tools for the detection of matching base pairs. It has been found that single DNA strands form double-strands in a slight excess of target strands, even if a few mismatches were introduced.

Inhibiting the quorum-sensing between bacteria is also a promising approach. Therefore, modified and functionalized furanones are used to inhibit biofilm formation through interference with quorum-sensing of bacteria.

All current systems provide only continuous drug release to prevent implant infection whether bacteria are present or not. Such a constant unspecific release may lead to resistance effects, breeding bacteria in the implants and affecting normal tissue besides an enormous waste of drugs.

As the state of the art does not provide coatings, nanospheres or adhesions which inhibit colonization of bacteria on or at implants, in solutions, in solids or wherever bacteria could be present, the demand for systems to detect bacteria are in the focus, to indicate bacterial presence and provide defence mechanisms.

Furthermore all of the methods already known within the state of the art require much more drugs than actually required for defence mechanisms against bacterial infection and to inhibit bacterial infections and the formation of biofilms on implants and fixation devices.

Therefore the problem underlying was to determine bacteria, provide defence mechanisms and inhibit bacterial infections. Furthermore, the direct detection of bacteria, reliable indication and direct displaying of their presence was a further problem, which had to be solved.

It is further an object of the present invention to provide a compound and composition suitable to determine, detect and indicate the presence of bacteria, to provide a defence mechanism, which could inhibit bacterial infections and the formation of biofilms, allows a reduction of the necessary amount of drugs while minimizing the risk of breading drug-resistant bacteria.

In addition to that a compound and a composition suitable to determine bacterial infections as well as a method to manufacture the compound and composition are provided.

Surprisingly it has been found that it is possible to detect, determine and indicate the presence of bacteria with an antimicrobial system equipped with a scaffolded sensor.

The sensor according to the invention detects the presence of bacteria, which triggers a conformational change of the intrinsically metastable scaffold to an energetically more stable conformation.

In the sense of the present invention a "sensor" shall be understood that a trigger for the conformational change of the scaffold can be the presence of bacteria, a virus, germs, moulds, fungus, metabolic or waste products, metabolic or waste product of any microbe or bacteria, peptides, amino acids, toxins, toxic substances, microbes, spores, disease-genes, any environmental change such as temperature, pH, ion concentration, magnetic influences, irradiation, such as UV-, IR-, α-, β-, γ-, X-ray-radiation, microwaves, pressure, osmosis, concentration gradients etc. The sensor according to the invention could thus also be designated as "bacterial sensor", "biochemical sensor" and/or "biophysical sensor", preferably as "bacterial sensor".

The term "ligand" as used therein is understood, that it can be as being a chemical entity which functions as a substituent, which can be attached or bound to a scaffolded sensor. Ligands can be either (unreactive) ligands, such as RNA-strands, DNA-strands, peptides, amino-acids, enzymes, substrates, complexes etc. to enable a hybridization whenever an at least partly matching complementary RNA-strand, DNA-strand, peptide, amino-acid, enzyme, substrate, complex etc. is present, or ligands which can react as participant in a chemical reaction (reactive ligands). The ligands are selected from the group of reactive or non-reactive ligands, DNA- and/or RNA-strands, sugars, peptides, amino acids, enzyme-substrate-complexes, or enzymes or substrates, organometallic and coordination compounds, compound-filled containers, functionalized ligands, alcohols, indicators (e.g. pH-indicators which can change their colour due to a change of the pH-value).

Any sterical demanding ligand can be attached to the scaffold either functionalized with functional groups, DNA and/or RNA, or any other metal or compound.

Preferably, a ligand is a reactive compound, a DNA and/or RNA-strand, to detect bacterial DNA and/or RNA or other bacterial compounds, metabolic or waste products, besides other detectable compounds such as sugars, peptides, peptide-PNAs, molecules, derivatives, amino acids, metal-complexes, metalorganic-compounds, enzyme-substrate complexes or parts of the latter which are equipped with either a functional group, specific for its type or any other structural design which enables the substrate to interact with any ligand of a scaffold according to the present invention.

Furthermore, the ligand can be sterically demanding or non-sterically demanding.

The term "locking-ligands" describes a pair of ligands, that are attached to the scaffold and by mutual interaction hold the scaffold in an energetically unfavoured conformation.

The term "substrate" according to the present invention is understood as being any substance e.g. DNA-, and/or RNA-strands, amino acids, peptides, sugars, bacterial components (polysaccharides) or microparticles of bacteria or material debris, metabolic or waste products, quorum sensing, toxic substances, disease-genes, enzyme-substrate complexes or any other compound, detectable with the scaffolded sensor.

The term "compound" according to the present invention is understood as being a group of drugs, antibiotics, metal salts, e.g. sulfates, sulfides, sulfazines, sulfadiazines, indicators, denaturating agents, metalorganic complexes, buffers, alcohols, magnetic compounds, vesicles.

The term "container" as used herein means a porous usually hollow nanocapsule made of an inert material, like for example fullerenes, inorganic oxides like silica, alumina, silica-alumina compounds etc. The manufacture of such container is described further below.

The term "nanocapsule" as used herein is a porous nanocapsule, which has the possibility to change the pore size reversibly. Among the known containers, polymer-based containers as well as oxidic materials have been studied in order to synthesize hollow nanocapsules. Given the robustness of the oxidic compounds and their biocompatibility e.g. for $TiO_2$, $SiO$, $SnO_2$, $Al_2O_3$, $AlO(OH)$ or metal-based compounds. Preferably, the outer shell of the nanocapsules provides an anti-bacterial activity, especially an anti-inflammatory and anti-infective activity when applied in coatings of implant devices implants, or surgical equipment and instruments, reservoirs for liquids or other material that should be sterile.

It is another object of the present invention to provide a method, compound and composition to detect bacteria, virus, fungus, spores, mould, germs, disease-genes, toxic substances etc. in solids, solutions, in vitro or in living tissue with a sensor with an intrinsically metastable scaffold. In a further mode of the invention, the scaffold can be linked to drug-filled containers to trigger drug release to defeat the present bacteria.

By the inventive method, the presence of bacteria can be directly detected, which results in a conformational change of the metastable scaffold. The change into an energetically more stable conformation can be displayed and detected for example by a change in colour of the sensor, an emission of light (visible or non-visible), an increase of temperature, a release of chemicals, gaseous, liquid, smelling, bubbling or fluorescent, odorant, foul tasting.

In a further mode of the invention, the release of chemicals can be a drug release from a container linked to the scaffold, to inhibit a bacterial infection, inflammatory, formation of biofilms and adhesions. The sensor enables to release exactly the amount of drugs necessary to fight the present bacteria, at their place of origin, without wasting drugs, risking inactivity due to slow or inhibited release from the container, affecting healthy tissue or risking bacteria resistance due to constant drug release. Furthermore, the antimicrobial system can detect bacteria and indicate the presence, by detectable or visible signals, e.g. changing color, or conductivity etc. Furthermore, a high sensitivity to the kind of bacteria is provided which enables an optimized medical treatment of the bacterial infection, and a short-term detection of the disease. In particular, implants can be provided with such inventive compounds, to inhibit infections directly and prevent inflammatory or rejections of implants, fixation devices, or organ transplantations, and prevent the formation of biofilms due to bacterial infection, to increase the survival rate and enhance the healing of patients.

The scaffold of the sensor according to the present invention registers the presence of bacteria due to present substrates e.g. DNA-, and/or RNA-strands, amino acids, peptides, sugars, bacterial components (polysaccharides) or microparticles of bacteria or material debris, metabolic or waste products, quorum-sensing, toxic substances, disease-genes, enzyme-substrate complexes or any other compound, detectable with the scaffolded sensor. The presence of such substrates triggers a conformational change of the metastable scaffold. Therefore a direct detection is provided to obtain reliable results whether bacteria are present or not.

The intrinsically metastable conformation of the scaffold is held in its unfavoured conformation unless the scaffold is triggered by any trigger, to undergo a change into an energetically more favoured conformation. The pairing of the locking-ligands, either reactive or non-reactive ligands, forces the scaffold in its unfavoured position. The pairing or binding of the locking-ligands breaks whenever any substrate is present, due to a higher binding energy between the substrate and one of the locking-ligands.

In a further embodiment of the present invention the pairing of the locking-ligands results from at least partly mismatching DNA and/or RNA-strands. But any other substrate-sensitive ligand known to a skilled person can be applied.

A conformational change to an energetically more favoured conformation can be triggered by a change in temperature, pH, ion-concentration in the environment, presence of different compounds such as, sugars, peptides, metabolic or waste products, substrates, amino-acids, enzymes, enzyme-substrate complexes, or any bacteria, virus, germ, mould, fungus etc.

Whenever a substrate is present the pairing of the locking-ligands breaks, due to the better matching substrate, which binds to one of the locking-ligands. The break of the interaction between the locking-ligands initiates a conformational change into a more favourable conformation which triggers a subsequent process. In a specific mode of the invention such a subsequent process can be the chemical reaction occurring between the freed ligand and another ligand attached to the scaffold, e.g. an elimination reaction, which results in eliminating ions or molecules e.g. leaving groups or halides of the other ligand bound to the scaffold. Due to the chemical reaction the more stable conformation is reached and stabilized. The elimination of ions or neutral molecules, e.g. leaving groups leads to a change of concentration in the environment of the scaffold, which can initiate further reactions, e.g. the release of other compounds, other changes in the sensor e.g. change in colour, temperature, pH, ion concentration, emitting light, gas, or liquids.

In a further mode of the invention, the conformational change of the scaffold due to the new binding to the substrates triggers an increased temperature of the sample resulting from releasing binding energy due to a higher binding energy of the new pairing. This has the beneficial effect that a change in temperature can be easily detected via thermistors etc., besides inhibiting a further infection of bacteria, which are highly temperature sensitive. Used for medical purposes, an increase in temperature supports the body's own defence mechanism, resulting in a more effective battle with bacterial infections.

In still another embodiment of the invention, due to the change in ion concentration resulting from the elimination of the leaving groups, the bacterial infection can be inhibited, while further changes can also be initiated, if the sensor is equipped with e.g. a nanoporous drug-filled container, the release of the drug can be initiated due to increased pore sizes of the containers, based on the solutions tendency towards creating an equilibrium between the different concentrations.

The eliminated small molecules can further trigger a pH-change of the sample, resulting in a change of colour, when indicators are either attached to the scaffold or released from a container linked to the scaffold. Chemical indicator reactions lead preferably to colour changes which can be easily detected and indicate therefore reliably the presence of the trigger.

The eliminated small molecules can further react with other ligands, trigger the release of other compounds, e.g. attached indicator molecules (e.g. pH-indicator molecules which can change their colour due to a change of the pH-value) or drugs to prevent further bacterial infection. Therefore, the battle with bacteria can be directly initiated by the presence itself. The colour change is helpful to indicate bacteria or any other substrate, such as mould, germ, virus, microbial etc. to prevent usage of the infected sample.

The conformational change triggers the release of compounds either directly or indirectly. Directly, via elimination of linked ligands, or indirectly via release from attached containers. Furthermore gases can also be released either directly or indirectly, which also initiates a colour change or taste of the sample, containing the sensor. Besides a colour change, also any other visual detectable change can be triggered, such as emission of light, fluorescence etc. Besides that, the release of ligands can defeat the environmental influence, which has caused the conformational change.

Another embodiment of the present invention enables triggering of any substrate in solids, solutions etc. by providing a visual signal when the metastable conformation changes into an energetically more stable conformation. Therefore, visual signals can be a change in colour of the solution, solid, etc., the formation of gaseous bubbles, which indicates the presence of any substrate related to bacteria, virus, germ, spores, mould, disease-genes, toxic substances etc. A colour change, denaturation or any other indication for the presence of a detected substrate provides good protection against infections or illnesses.

In another embodiment of the present invention, the scaffolded sensor is equipped with a container comprising a drug for triggering drug release, wherein the scaffold is intrinsically metastable. With the scaffolded sensor, the presence of bacteria is detectable, which initiates the release of drugs from a container comprising a drug, to inhibit the formation of biofilms on e.g. implants, and especially infections of the detected bacteria.

Such drug filled containers can comprise any drugs having an antimicrobial effect, or other effects on any disease imaginable by a skilled person. Inhibiting bacterial or virulent infections can be achieved by e.g. antibiotics, lactam-derivatives, metal derivates, of platinum, gold, bismuth, titanium, manganese, copper or silver compounds, such as silver nanoparticles, either functionalized with amino acid sequences, peptides or other derivatives effecting diseases, bacterial infects, virulent infects or other illnesses, peptides, sulfadiazines, or any such compounds known to a skilled person.

Not only drugs can be released from these containers, but also compounds to denature solutions or mark them as contaminated via release of coloured compounds, e.g. to indicate bacteria contaminated drinking water, to prevent consumption and illnesses caused by the bacterial infections.

Beneficially, the release of compounds from the containers is triggered by the presence of bacteria and therefore only released when and as long as bacteria are present. Therefore, the released amount, which is necessary to battle with a bacterial infection can be extraordinarily reduced.

In case of drug-filled containers, breading drug resistance of bacteria is prevented, due to a short-term application of drugs. In the state of the art, drugs, such as antibiotics are applied for long terms, to ensure the complete extinction of a bacterial infection. By the sensor according to the invention, the drug release is only provided in the presence of bacteria, fungus, microbes, spores, mould, disease-genes, toxic substances or any other germ and therefore stopped, whenever the bacterial infection is defeated.

According to the present invention the compound-filled containers are linked to a conformationally metastable scaffold. The metastable scaffold is forced into a less preferred conformation, which initiates a conformational change whenever bacteria are present. The change in conformation starts from a metastable conformation into a preferred stable conformation, which initiates the release of compounds from a container.

The compound is directly released to provide either inhibition of further bacterial infections, indicate the presence of bacteria due to a change in colour, when the released compounds are indicators, keep the sensor in certain places, in case of a magnetic compound, provides an emission of light, when the compound is a fluorescent, increases the samples temperature when the compound reacts with a ligand attached to the scaffold, wherefrom binding energy is released, or undergoes a chemical reaction with compounds already present in the environment. Therefore, the release happens exactly where the bacteria are present, and it is ensured that as few as possible drugs are used to defeat a bacterial infection as the presence of bacteria is needed to release the drugs.

The scaffolded sensor comprises at least one drug-filled container, which is linked to the conformationally metastable scaffold either by a linker or is directly bound. It depends on the kind of bacteria and the use if the containers are directly or indirectly bound to the scaffold. It is beneficial when the containers are equipped with tethers, via tethers a container can not only be linked to the scaffold but also to different surfaces. Such containers can therefore be attached e.g. to an implant material, either directly via such a surface tether or also on top of a previously deposited coating. Furthermore, containers can either be bound to the scaffold and also to a surface.

The container can be implemented in a coating by attaching it via tethers onto or into a surface. In there, slow compound release is provided, to assure the inhibition of bacterial infection. Attached to the surface of a coating, especially an implant or fixation device, infections due to bacterial settling is inhibited. Such coatings can also be applied to any medical or sterile object, to provide bacterial-free equipment. If such a sensor is attached to any surface, the formation of biofilms is inhibited.

Additionally, the compounds encapsulated in the containers can inhibit the formation of biofilms due to the presence of bacteria. These compounds are released and prevent the colonization of the bacteria in such biofilms. In case of the biofilm is already formed and colonized by bacteria, other compounds either directly linked to the scaffold or encapsulated in the containers can be released to dissolve the biofilms, and battle with the present bacteria. The compounds can be released to dissolve these biofilms, migrate into the biofilm-matrix, set there and prevent further formation and eliminate the biofilm-matrix. Furthermore, functionalized containers can be filled with bacteria selective compounds.

Whenever bacteria or biofilms are present the containers are separated by the conformational change of the scaffold, triggered by the bacteria, migrate into the biofilm-matrix, where they start to release the dissolving and antimicrobial compounds, directly in the matrix.

Usually, biofilms allow bacteria to resist antimicrobial agents, due to their colonization and proliferation in the biofilms which protects them of the antimicrobial compounds, it is almost impossible to treat formed biofilms with normal methods after formation. With the present method, the formation and therefore the infection rate can be extraordinarily decreased when biofilm-formation and proliferation of bacteria is inhibited.

Alternatively, without the sensor equipped with compound-filled containers can be directly embedded into a surface coating, either directly by application of mixed coatings, or via tethers. This is advantageous if implants are provided with such a coating, as it ensures that no inflammation or bacterial infection can occur after the surgery and accelerates the healing process. Such coatings can also be applied on surgery or medical equipment, or all compounds, which shall stay clean and aseptic.

As discussed the invention beforehand provides a sensor, which comprises a scaffold that has a plurality of changeable conformations. The scaffold is forced into a metastable conformation, which can be changed between different more or less energetically preferred conformations. The scaffold is intrinsically conformational metastable, which can be changed in the presence of a trigger.

The scaffold provides at least one metastable conformation and at least one conformational stable conformation. Such a scaffold might be a cyclohexane- or a ferrocene-derivate, or any compound which can undergo a conformational change, initiated by any environmental factor, such as pH, temperature, irradiation, such as UV-, IR-, $\alpha$-, $\beta$-, $\gamma$-, X-ray-radiation, microwaves etc., or the presence of an activator, intramolecular shifting, due to a reaction between bound ligands, which are linked to the scaffold, or an intermolecular shifting, resulting from a reaction between different molecules and certain ligands, bound to the scaffold. FIG. 1 shows schematically a sensor with a cyclohexane scaffold, forced into a conformational metastable state by functional groups.

The conformational change of the scaffold can be reversible, preferably it is irreversible. Advantageously the conformational change of the scaffold is easily initiated, while the amount of changed scaffolds depends on the intensity of the environmental change, which can easily be detected.

Such conformational changes can also be detectable by a colour change of the sensor. The presence of bacterial DNA and/or RNA or any other compound related to bacterial presence triggers the scaffolded sensor to change its colour, preferred in a range of visible light and releases drugs from a container. So, in the presence of bacteria, the less preferred metastable conformation changes into a more stable conformation, which leads to a colour change to display the conformational change.

Furthermore, in the presence of bacteria, the scaffold can trigger directly the release of chemicals to denature e.g. drinking water, food etc. to prevent infections due to consumption of bacteria contaminated food, drinks, etc. Another method, to prevent consumption of contaminated food is when the sensor detects bacteria and triggers release of smelling or bubbling gas, foul tasting, initiates a change in colour of the sensor composition, results in a change of colour of the solution, solid etc. which can be released from attached containers. Therefore, the attached sensor secures in an effective way that the contaminated food, water, drink etc. does not lead to a bacterial infection.

The conformational change can also trigger a direct release of chemicals, either to defeat the present bacteria, or denature the solution, solid etc.

In addition, the conformational change can trigger the release of compound-filled containers, either functionalized to provide the release of compounds directly in, on or at coatings or adhesions, either do defeat the presence bacteria, denature the solution, solid etc. or to indicate the presence by a change of colour due to the release of indicators, dyes, pigments etc. which can be attached to the infected surface of a coating or adhesion.

In another embodiment of the present invention the sensor can also detect the presence of other germs, virus, fungus, spores, mould, disease-genes, toxic substances or any other problem, which can cause illnesses, sicknesses or can affect human health.

In the sense of the present invention the scaffold of the sensor can be for example a cyclohexane- or a ferrocene-derivate or any skeletal structure to which different ligands can be bound, either reversible or irreversible. Preferably the scaffold provides a three-dimensional structure, with an ability to provide conformational changes. Advantageously, the scaffold itself is an inert compound, and shows good biocompatibility.

Figure 5:
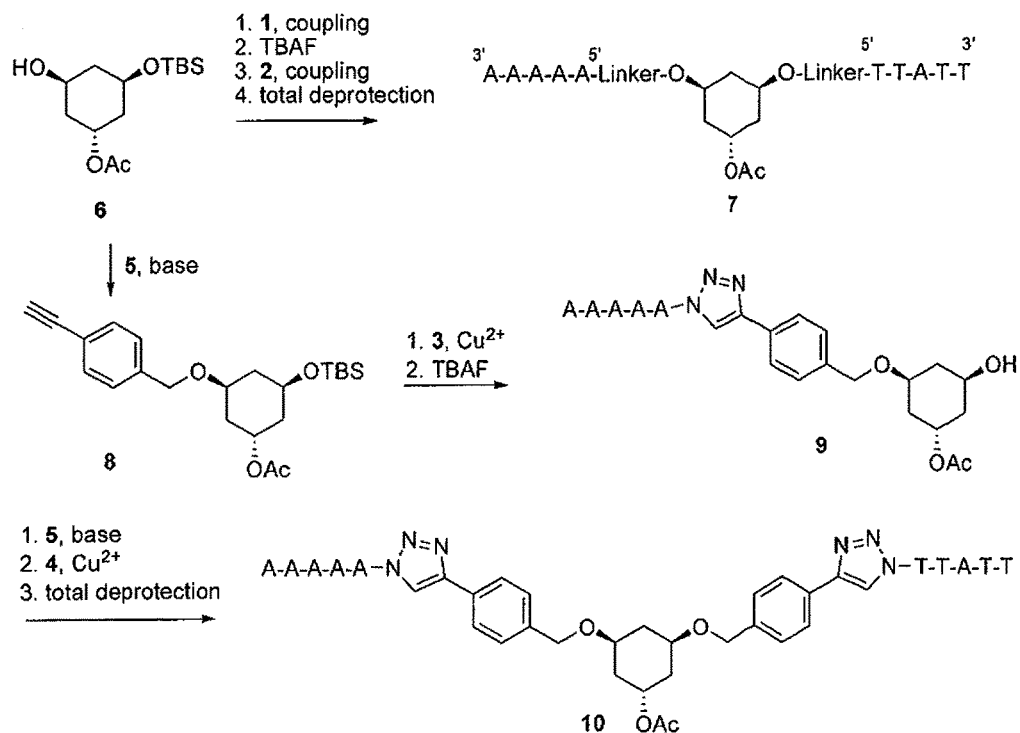

The sensor according to the invention comprises a scaffold, which preferably provides a plurality of conformations, for example a cyclohexane-derivate. The advantageous is that cyclohexane-derivates are quite unreactive and nontoxic and provide a plurality of different conformations, such as the chair, half-chair, envelope, twist or twist-boat or boat conformation. Only the twist form is isolable as—like the chair conformation—it represents a preferred energetic state, an energy minimum. The boat conformation does not suffer from angle strain but has a higher energy than the chair form due to steric strain resulting from the two axial 1,4-hydrogen atoms, in what is called the flagpole interaction. The torsional strain in the boat conformation has a maximum value because two of the carbon bonds are eclipsed. Compare this to the chair with all bonds staggered and complete absence of torsional strain and the twist-boat with 4 out 6 bonds partially eclipsed. In the half-chair conformation four carbon atoms are located on a plane in which two bonds are fully eclipsed. The boat and envelope forms are transition states between the twist forms and the twist and chair forms respectively, and are impossible to isolate. The twist-boat conformation is less stable than the chair conformation. The ring flipping process can now be described with more precision as taking place through a twist-boat conformation and through two half-chair transition states. Although not stable at ambient temperatures, all conformations can be stabilized when ligands are introduced. An exemplary synthesis route of a cyclohexane scaffold with attached ligands is shown in FIG. 5.

Figure 6:
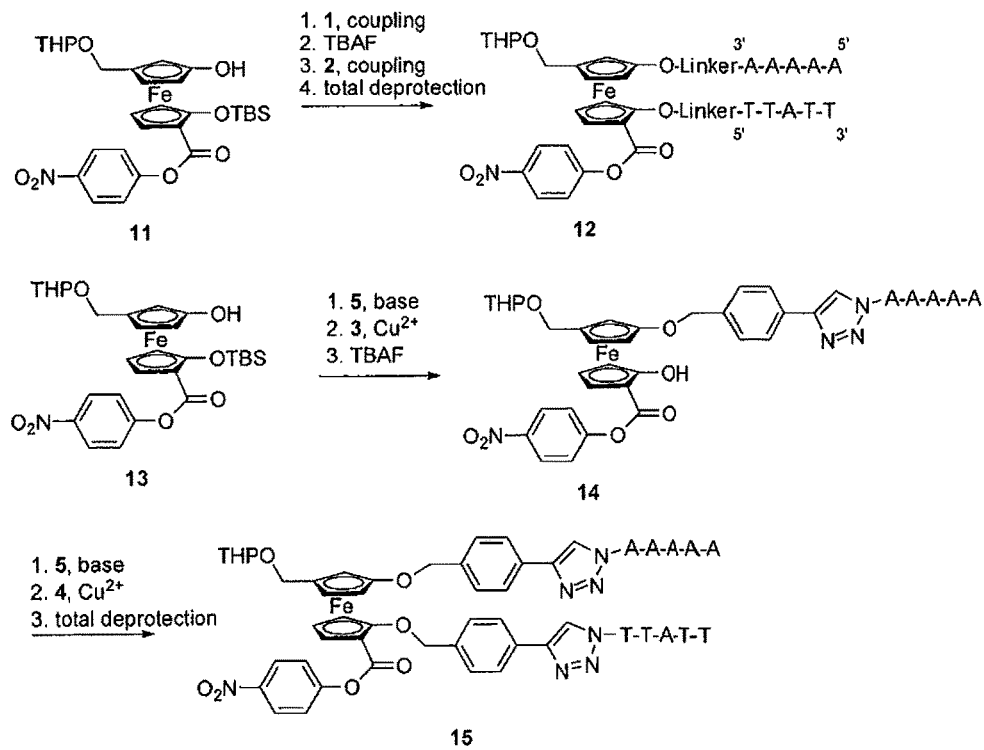

Another modification of a sensor according to the present invention uses a ferrocene-derivate as scaffold. The ferrocene-derivate shows rotationally flexible cyclopentadiene rings, which can stand either in a staggered conformation or eclipsed conformation. The advantage of applying such scaffold-derivatives is that the conformation can change very easily, but can be stabilized by rotation-inhibiting ligands. Therefore the conformational change of the scaffolded sensor is initiated very easily by any change of the environmental factors. An exemplary synthesis route to a ferrocene scaffold with attached ligands is shown in FIG. 6.

The change of the scaffold of the bacteria sensor can also be initiated by the presence of bacteria. It can also be initiated by bacterial cell wall constituents or other signalling molecules. Detection of bacteria can be effected via present DNA and/or RNA or any other bacterial compounds or products in the environment of the sensor. The scaffold of the sensor can be equipped with matching or mismatching, or at least partly mismatching DNA and/or RNA sequences, which have the function of detecting bacterial DNA and/or RNA fragments or sequences in the environment. The matching of the bacterial DNA and/or RNA sequences with DNA and/or RNA initiator-sequences linked to the scaffold trigger the conformational change of the scaffold. Therefore the detection of the bacteria in the environment of the sensor is directly initiated by the presence of bacteria and is detected without time loss.

The matching of the bacterial DNA and/or RNA sequences with DNA and/or RNA initiator-sequences linked to the scaffold trigger the conformational change of the scaffold, while the conformational change triggers drug release from the containers. Therefore bacteria are detected and defeated in the same time, without any further test, diagnosis or any other treatment. So, the amount of drugs can be reduced to the actual necessary amount, the effectivity is increased as the drugs are directly released where needed, and the risk of breading drug-resistant bacteria, e.g. to antibiotics, is dramatically decreased, as the presence of the bacteria triggers the drug release.

The scaffold of the sensor has ligands. Such ligands can be ligands, which can be attached to the scaffold. Suitable ligands have been described in the foregoing.

Furthermore, tracing systems can be attached to the scaffold, to determine the effectivity of the sensor, which can be detected with any device known in the state of the art.

The ligands can be axially arranged, so that the conformation of the scaffold is forced into the metastable conformation. The ligands can thereby force the scaffold into the metastable conformation by a bonding of the locking-ligands, e.g. matching, mismatching or partly mismatching DNA and/or RNA strands. A conformational change of the scaffold can be initiated by the breaking of the interactions of the locking-ligands. As they stabilize the metastable conformation of the scaffold, due to a release of the binding between the ligands the conformation can change to a more stable position, as the position of the ligands is rearranged and can flip into equatorial positions. If the metastable conformation switches to a more stable conformation, the other ligands are in close proximity to each other. Therefore an intramolecular chemical reaction with another ligand nearby can occur, or intermolecular reaction with a ligand or any other compound, or activator present in the environment resulting in a more stable conformation of the scaffold.

Figure 2:
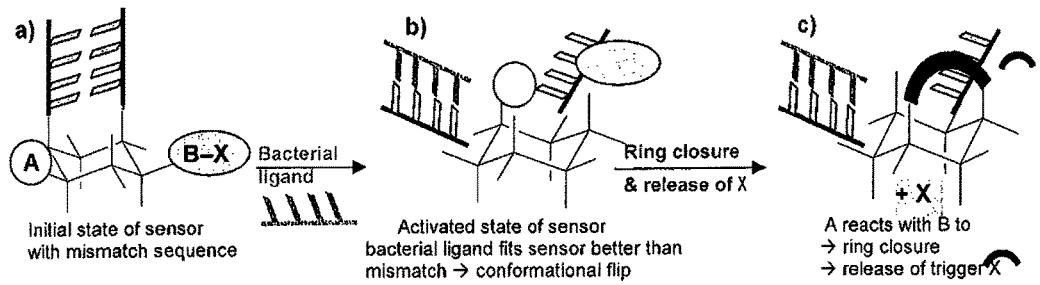

In an embodiment, the sensor in the sense of the invention has a scaffold with at least one ligand and at least a partly mismatching pair of DNA and/or RNA strands as exemplified in FIG. 2. The scaffold of such a bacteria sensor is kept in an intrinsically metastable conformation by the interaction of at least two complementary strands of DNA and/or RNA, which show some degree of mismatching. In the presence of a fully matching complementary single-stranded sequence in solution or in the environment, a stronger interaction will result, a so-called hybridization of the DNA and/or RNA strands, thus breaking the intramolecular pairing of the mismatching DNA and/or RNA and initiate a conformational change. Thus, the spatially more appropriate equatorial positioning of both DNA and/or RNA-strands (one of them now as a duplex with the foreign complementary sequence) will force other parts of the ring to be in close proximity and allow an intramolecular chemical reaction, releasing X (by-product). The two ligands, the DNA and/or RNA-strands are forced into more stable equatorial positions, initiating the release mechanism, as they place the conformation in the relevant conformation, in that way, that the elimination can proceed.

Figure 3:
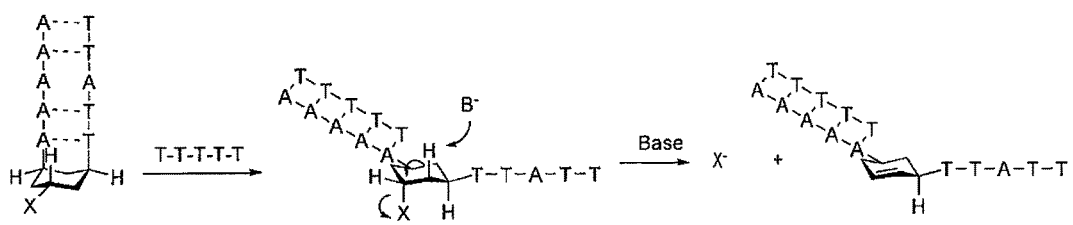

More specifically, such a reaction can be a lactonization (X=alcohol or F, see also FIG. 3) or a trans $E_2$-elimination (BX=halide), depending on the functionalized group. A ligand attached to the scaffold is then a reactive ligand, which can be functionalized with an alcohol, halogen or any other leaving group.

In this concept, any kind of molecular recognition types e.g. peptides, small molecules and other types of nucleic acids can be applied.

Figure 4:
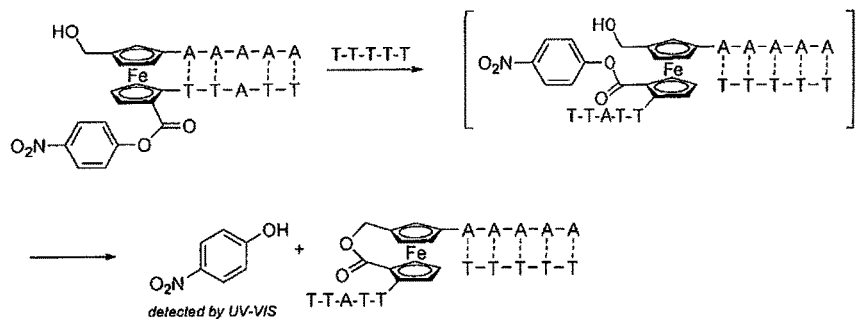

Further, the exploitation of the rotational freedom of a ferrocene-scaffold-derivate is restricted by the intramolecular DNA and/or RNA partly mis-matching DNA and/or RNA strands, but hybridization of a fully matching with a foreign DNA and/or RNA-strand releases the restriction and the conformation can rotate and switch into an energetically more convenient conformation as is shown exemplarily in FIG. 4.

As DNA and/or RNA-sequence, every sequence known to a skilled person can be applied and attached to the scaffold of the sensor. Non-limiting examples are the sequences AAAAA and TTATT, but also better matching sequences, or other sequences, which are more convenient or cheaper. The sequence must be adapted to the kind of bacteria, which shall be detected.

Furthermore, imide/aminopyrimidine systems, can be attached, or sequences such as AAGGAGGTGA and/or GTTACGACTTCAC and the at least partly mismatching partner strand, e.g. mRBS-0 (($KFF)_3K$-$(egl^d)_2$-AAGGAGGTGA), mRBS-1 (($KFF)_3K$-(egl)2-AAGGACGTGA), mRBS-2 (($KFF)_3K$-(egl)2-ACCGAGGTGA), 344 (($KFF)_3K$-$(G^e)$ -GCTGCCTCCCGT), 522 (($KFF)_3K$-(G)-TTACCGCGGCTG), 899 (($KFF)_3K$-(G)-GAGTTTTAAC-CTTG), 1489 (($KFF)_3K$-(G) GTTACGACTTCAC).

As outlined before the sensor comprises at least one ligand, which is preferably a container. A container can be a drug-filled container. Such drug-filled containers can be provided with different antimicrobial compounds depending on the application area and the kind of bacteria, which shall be defeated.

The compounds filled in such containers are only limited by their size and solubility. Beneficially, compounds with an antimicrobial effect are filled into the containers.

As drugs, different compounds can be applied in dependency of the expected kind of bacteria. But also metal salts can be used to inhibit bacterial infections, e.g. silver ions, such as silver sulfadiazines are filled into such containers. Silver compounds are due to their bacteria cytotoxicity highly appreciated.

Besides silver compounds different other inorganic or organic metal compounds can be applied which provide good solubility, high efficiency and less undesirable side effects. Applicable are compositions, comprising Pt, Cu, Bi, Au, Ti or mixtures thereof. Advantageously, antimicrobial silver, bismuth, copper, gold compositions are applied, e.g. Cu-salts, colloidal bismuth subcitrate (CBS), bismuth subsalicylate (BSS).

As the scientific world supposes that bacteria cannot become resistant to silver due to its non-specific enzymatic interference with a number of bacterial enzymes, a silver application is advised in cases of antibiotic-resistant bacteria. The molecular mechanism of action of silver ions leads to an effective preferential binding for silver ions and silver nanoparticles in bio-molecules. Silver ions are preferentially recognized and bound by certain amino acid sequences or peptides.

Therefore, silver nanoparticles of defined size were formed as a function of these amino acid sequences. Silver compounds may be engineered as a function of peptides, to inhibit bacterial infections. Furthermore, antimicrobial compounds formed with silver ions and peptide-based antibiotics, e.g. vancomycin are also applied in defeating bacteria.

As the solubility of silver-compounds is still a demanding challenge, the implementation of silver-compounds, e.g. silver-salts, into containers solve this problem. Filled into containers and released when needed, the silver-compounds affect the present bacteria and inhibit their reproduction. Solubility is therefore no longer a problem, as only small amounts are released from the container over a long period of time.

The implementation into containers is only limited by the size of the compounds therefore not every compound can be transported into the containers. The metal-derivatives used as antimicrobial drugs should further provide good binding properties to the bacterial cell wall molecules to certain polysaccharides or proteins, as they interfere by displacing essential ions, such as $Ca^{2+}$, $Zn^{2+}$ from enzymes vital for bacterial respiration and growth. Additionally platinum-, gold-, manganese-compounds or even some peptides have also been successfully applied due to their binding properties toward silver ions, and the silver binding ones do indicate a preferential enrichment of proline and hydroxyl-containing amino acid residues. Furthermore, silver can remain for an extended period in the body without harming the tissue, which was successfully affirmed in long-term studies. Therefore, the effect of silver compounds applied as nanoparticles or (nano-) powders was investigated. Silver metal compounds were applied in vivo subcutaneously, but the release from containers is more effective. The latter provide confined space for a silver compound and allow a slow and constant release of the latter via diffusion.

Furthermore, the investigation of the cytotoxicity of silver nanoparticles and silver acetate with human mesenchymal stem cells (hMSC) was found to be cytotoxic due to cell reactions occurring for nanoparticles for silver acetate, while MIC of silver for yeast, *E. coli* or *S. aureus* are much lower. Another effect of silver nanoparticles is to reduce the ability of blood platelets to clump together with no harmful side effects. Antimicrobial coatings containing at least 1-5% silver nanoparticles e.g. in combination with hydroxyapatite, showed neither cytotoxicity nor hemolysis.

As discussed beforehand, the scaffold's conformational change is triggered by the presence of bacteria. The scaffold is functionalized with ligands, which can be DNA and/or RNA-strands or any other compound which can bind to amino DNA and/or RNA, sugars, enzyme-substrate complexes or parts thereof, amino acids, peptides or any other metabolic or waste product. The scaffold is kept in a metastable conformational state by the interaction of complementary strands of DNA and/or RNA, with some degree of mismatch. The partly mismatching DNA and/or RNA-strands force the conformation of the scaffold into an energetically unfavoured metastable conformation. In the presence of a matching complementary bacterial strand of DNA and/or RNA, which is a fully matching complementary single-stranded sequence, a stronger interaction will result, a so-called hybridization of the DNA and/or RNA-strands, thus breaking the intramolecular pairing of the partly mismatching DNA and/or RNA-strands, initiating a conformational change. The conformational change triggers a chemical intramolecular or intermolecular reaction, which initiates drug release from the drug-filled container, linked or bound to the scaffold. As the sensor is sensitive to bacterial DNA and/or RNA, drug release is only initiated, in the presence of bacteria.

Therefore, the drugs are only released in presence of bacteria, to enable a final destruction of bacterial colonization and infection with a low risk of bacterial drug-resistance. Furthermore, the sensor can be modified in that way, that specific types of bacteria can be detected and indicated, e.g. by changing the colour, conductivity or pH of a solution. A sensor, equipped with a scaffold, sensitive to the presence of bacteria or any other virus, fungus, mould, disease-genes, toxic substances or any other germ can also prevent the formation of biofilms due to bacterial infection, and provide better healing of patents with implants, fixation devices or after transplantations. Furthermore, in absence of bacteria the drug release is stopped or slowed down, while drug release is increased in the presence of bacteria.

Not only the presence of bacterial DNA and/or RNA can trigger a conformational change of the scaffold, but also any bacterial compound, such as specific amino acid sequences or peptides, besides bacterial metabolites or waste products or quorum sensing molecules.

The sensor triggers the conformational change of the scaffold, which initiates an intramolecular chemical reaction of the reactive or non-reactive ligands. A conformationally intrinsically unstable scaffold is kept in a metastable state by the interaction of complementary strands of DNA and/or RNA, with at least some degree of mismatch. In the presence of a fully matching complementary single-stranded sequence in solution, a stronger interaction will result, thus breaking the intramolecular pairing and trigger a conformational change. Thus, the spatially more appropriate equatorial positioning of both DNA and/or RNA, one of them now as a duplex with the foreign complementary sequence, will force other parts of the ring to be in close proximity and allowing an intramolecular chemical reaction, releasing small molecules, e.g. halides or other leaving groups. More specifically, such a reaction could be a lactonization, with alcohol or halides as leaving groups or a trans E2 elimination. This mechanism is not limited to DNA and/or RNA strands, any kind of molecular recognizable type, e.g. peptides, small molecules and other types of nucleic acids could be applied in this method.

A conformational change of the scaffold can be initiated by the breaking of the interactions of the locking-ligands. As they stabilize the metastable conformation of the scaffold, due to a release of the binding between the ligands the conformation can change to a more stable position, as the position of the ligands is rearranged and can flip into equatorial positions. As a consequence of the conformational switch into a more stable conformation, the other ligands are in close proximity to each other. Therefore an intramolecular chemical reaction with another ligand nearby can occur, or intermolecular reaction with a ligand or any other compound, or activator present in the environment It was found that an intramolecular chemical reaction triggers drug release from the container. When bacteria are present, the conformational change of the scaffold is triggered, which initiates the intramolecular chemical reaction of ligands, bound to the scaffold. The intramolecular reaction of the ligands can trigger drug release from the containers. Therefore, only in the presence of bacteria the conformational change is triggered which leads to an intramolecular reaction of the ligands and a release of drugs from the drug-filled containers to inhibit a bacterial infection. Therefore drugs are only released when and as long as bacteria are present, which reduces the necessary amount of drugs to prevent a bacterial infection, but increases also the activity of defeating the bacteria. As the release of the drug from containers is supposed to occur over a longer time, is applied in a better controlled way and in higher yield, while the sensor do not lose its effectiveness, as environmental changes do not lead to a decomposition.

Furthermore, such sensors equipped with drug-filled containers can be also linked to surfaces, covalently surface-linked coatings, or applied in coatings and have the advantage that they can be loaded with drugs after their grafting to surface coatings. The active part of the coating can either be incorporated into a passive matrix or form a layered structure together with the passive matrix. Nanoscale containers can be integrated into these coatings, from which slow, sustained or immediate release of the drugs from the containers is possible. Therefore different coatings can be applied, depending on the application field. Such as classical coatings are possible, consisting of sol-gels or pigments, passive host-active guest-structures into which the containers are incorporated, coatings providing a passive matrix to incorporate the containers or layered coatings having containers linked via tethers onto their surface. Loading of drugs into the shell possessing containers is done by controlled permeability properties, followed by the introduction of the drug-filled containers into the coating matrix.

The distribution is important as only an equal distribution provides secure drug release for inhibiting bacterial infections. Therefore passive matrix structures or any other passive coating is advantageously applied, for keeping the drug-filled containers in a trapped state to assure drug release is only provided when the environment undergoes the initiating changes. The release of the encapsulated drugs is initiated when environmental changes occur, and the nanocontainers respond to this signal. Beneficially, such coatings can be applied to any surgical equipment, implant or fixation devices, or any other surface, which shall be prevented from bacterial infection. Especially when linked to any coating or surface long-term stability is provided, as the sensitive drugs filled in the containers are not harmed.

Besides that, providing drugs in containers with such sensors shows the advantage that the timing of drug loading of containers is simplified. The application of sensors on surgical equipment e.g. can be chosen to take place before or after sterilization techniques, e.g. autoclaving, or any other technique to provide sterile equipment. In contrast to a direct application of antibiotics, a sensor, equipped with drug-filled containers shows no temperature-sensitiveness, even when antibiotics are provided in the drug-filled containers. Therefore, normal techniques to provide sterile equipment can be combined with coatings containing sensors or having sensors attached to the surface to prevent bacterial infections. A combination can lead to a lower infection rate in medical or surgical treatment or any other possible situation or device where sterility is needed.

An additional advantage of drug administration via sensors with scaffold-linked containers is that drugs filled into these containers resist to environmental influences such as temperature and pressure (e.g. in autoclaves), enzymatic activity or acidic conditions (e.g. when administered orally), losses due to diffusion (e.g. when applied directly in coatings) or any other destruction imaginable in a human or animalistic metabolism, body, solution, better than crude material which is directly administered or applied. Using sensors provide the advantage that the bacteria are directly detected and can be defeated by a release of the drugs from the drug-filled containers but provide also long-term stability, as they are very resistant to any environmental change.

As already explained before, the sensor has a container which is a porous nanocapsule filled with drugs. The sensor provides a scaffold linked to ligands, which can be at least one drug-filled container, which is a porous nanocapsule.

The nanocapsules demand materials having stable properties in a long-term range without inducing inflammation, or being decomposed in acidic, basic or neutral milieus. The nanocapsules are obtainable according to different methods known from the state of the art. Such material precursors consist of different inorganic oxide materials, often provided with a functionalized surface with different functional groups or metals or tethers to link the nanocapsules to coatings or surfaces. The hollow nanocapsules can be synthesized based on polystyrene latex beads, which are coated by sol-gel methods with the inorganic oxidic or functionalized material precursor. Subsequently, the inner part consisting of inorganic polystyrene latex beads which is destroyed by heating, e.g. calcination. So, only the outer part remains, resulting in hollow, porous inorganic oxidic shells. An alternative route provides a $SiO_2$ precursor, with nanoscale cores. After the deposition of the oxidic precursor nanoemulsion onto the $SiO_2$ precursor the silica is dissolved with NaOH. An inorganic shell remains then as hollow nanocapsule with a porous structure. The particle size, the thickness of the shell and the size of the pores can be adjusted by the different synthetic conditions. Another method uses microemulsions, building up the inorganic shell at the interface between the two phases, and result also in hollow nanocapsules. The resulting nanocapsules are sinter-stable, thermostable and are not soluble to maintain the integrity of the system. Ideally, the containers filled with drugs encapsulate and isolate them from foreign influences. Therefore, the drugs in the containers are long-term stable, in contrast to a direct application of drugs. Furthermore, the efficiency is increased as no losses appear due to metabolism e.g. or dilution.

Additionally, the nanocapsules can be equipped with tracing-systems, which can be a radioactive compound or any other compound to track the effectivity of the nanocapsules. Therefore on the outer shell, the nanocapsules can be functionalized further. The resulting nanocapsules obtained according to these methods, are porous. Preferably the size of the pores lies in between 0.5 nm and 500 nm.

Advantageously, the nanocapsules are high-temperature-stable containers, which provide hollow sphere encapsulation of drugs to inhibit bacterial infection in vivo or in vitro.

These nanocapsules can easily be filled either during the processing using microemulsions, or after processing via a vacuum technique. The latter process is possible due to the porosity of the oxide materials used. Nanocapsules are placed under vacuum and then soaked with a saturated solution of the compound, which is desired to be loaded into the nanocapsules. Nanoporosity allows these compounds to be absorbed inside the capsules, which are then filtered off by centrifugation, rinsed and dried. Molecules as large as 8-hydroxyquinoline have been absorbed in this way. These hollow nanocapsules are filled with compounds which show preferably antimicrobial effects, e.g. antibiotics, silver-compounds or mixtures thereof, or if applied to combat any other disease, any active component known to a person skilled in the art can be inserted. However, the insertion of the compound is only limited by the size of the pores of the porous nanocapsule. The nanocapsules provide confined space for a drug and allow a very slow release of the latter via diffusion through pores present in their shell.

The term "nanocapsule" as used herein is a porous nanocapsule, which has the possibility to change the pore size reversibly.

Among the known containers, polymer-based containers as well as oxidic materials have been studied in order to synthesize hollow nanocapsules. Given the robustness of the oxidic compounds and their biocompatibility e.g. for $TiO_2$, SiO, $SnO_2$, $Al_2O_3$, AlO(OH) or metal-based compounds. Preferably, the outer shell of the nanocapsules provides an anti-bacterial activity, especially an anti-inflammatory and anti-infective activity when applied in coatings of implant devices implants, or surgical equipment and instruments, reservoirs for liquids or other material that should be sterile.

The porosity of the nanocapsules can be influenced by the environment or solution surrounding the nanocapsules and the sensor. The pore size can either be changed by a conformational change of the scaffold of the sensor, initiated by the presence of foreign complementary DNA and/or RNA-strands, or other receptors such as bacterial amino acids, bacterial metabolism or waste products, peptides, by a change of the pH or conductivity due to the presence of bacteria or any other detectable change. The pores of the nanocapsule increase, to release a certain amount of drugs, but decrease and stop the release of drugs when the external influence (conformational change, pH or conductivity) disappears. The reversible opening and closing process of the pores guarantees that only a necessary amount of drugs is released to defeat the bacterial infection without risking bacterial resistance and wasting expensive drugs. Advantageously, the drug release results slowly and constantly, only as long as necessary and bacteria are present. A slow release enables the complete destruction of a bacterial population and inhibit infection and inflammation e.g. of tissue, implants, or solutions. The porous shells of the nanocapsules allow a very slow release of the latter via diffusion through pores present in their shell.

Furthermore, they can be grafted to surfaces or surface coatings via appropriate linkers (e.g. PEG) which are attached by functionalization of the surface. Such graftings can be attached to the nanocapsules, either all over the surface or only on one side of the nanocapsules. This can be realized e.g. by a Janus-type grafting method. This process consists in halfembedding the nanocapsules in a scaffold, such that the outside half can be functionalized with e.g. a surface tether or the linker to the sensor according to the present invention. The scaffold is then removed to set free the functionalized nanocapsules. Concerning the tethers, linker molecules are proposed, depending on the kind of surface onto which the nanocapsules are grafted. For a titanium surface, an acid function, similar as for $TiO_2$ itself, will be needed in terminal position.

The sensor can either be attached to an antimicrobial system, in the sense of the present invention the sensor can also be attached to other surfaces. Preferably the surface of the nanocapsules can be functionalized with antimicrobial metals, such as silver, gold, bismuth, titanium, platin. Inventive nanocapsules are attached to the implant material, either directly via a surface tether, on top of a previously deposited coating, or else embedded into a surface coating. In the first two cases, a surface tether is required. Such surfaces can also be metal surfaces, which are provided directly with a sensor, any coating known by a skilled person, or other application may provide the sensor directly in solutions. These metal-containing surfaces can be further functionalized with various groups, to provide even better antimicrobial effects. For a gold- or silver-containing surface, sulphur groups, either as single tether or as tripod, will be suitable. If the nanocapsules are to be deposited on an already coated implant, the functionality depends on the coating. As an example, on a titanium implant, which is coated with a coordination polymer, the adequate linker unit would best be a pyridyl moiety.

Furthermore, the nanoporous containers can regulate the release of the encapsulated compound due to an exchange of fluids between two solutions of different concentrations by means of nanopores in the containers. The solutions have a tendency towards creating an equilibrium between the different concentrations which is influenced by the encapsulated compound. In a special embodiment of the present invention the encapsulated compound can be a functionalized silver compound, e.g. a silver sulfazidine. In the presence of bacteria, virus, fungus, mould, disease-genes, toxic substances or other germs, or any detectable metabolic or waste product thereof, peptide, amino acid, substrate, enzyme, DNA and/or RNA or any other detectable compound, the scaffold changes its conformation, initiating a chemical reaction between the ligand, as described above.

Via elimination, halides are eliminated, which triggers the release of the silver-compound via diffusion from the attached container. Therefore, the released amount can be regulated by the concentration of the halide, e.g. chloride, fluoride etc. in the presence of the scaffold, either increased or decreased via regulation of the concentration due to the formation tendency of the silver halide.

A sustained release is possible from the nanocapsules with a slow kinetic in accordance with the intensity of the bacterial infection. Therefore only a minimum of drugs is needed to defeat the infection, reducing costs and resources.

The change in the pore size is induced by environmental factors. When environmental factors undergo certain changes, the containers respond to these changes, by increasing or decreasing their pore size. Such factors can be a change in the pH, temperature, different compounds which correspond to the sensor or any other activator.

In the presence of bacteria, the scaffolded sensor undergoes a conformational change affecting also the linked nanocapsule. Due to the close proximity of the ligands resulting in an intra- or intermolecular chemical reaction the container is affected by increasing its pore size to release the encapsulated drugs. Therefore the encapsulated drugs can be released to defeat the present bacteria.

Using inorganic nanocontainers has the advantage that a decrease of pH, as e.g. induced by the presence of bacteria, can increase the pore size of the nanocapsules to enhance drug release. However, it has been shown that small $TiO_2$-nanoparticles tend to agglomerate more if the pH sinks progressively from 10 to $2^{13}$. Such behaviour leads, in the case of hollow nanospheres of $TiO_2$, to the formation of larger pores in the shell wall. Other applicable compounds are AlO(OH), $SiO_2$, $Al_2O_3$, $CeO_2$, $Fe_2O_3$, $Fe_3O_4$, $Co_3O_4$ used as containers show a pH-dependency which remains a useful trigger for releasing drugs from drug-filled containers. The larger pores in the shell wall enable the release of the encapsulated drugs. Therefore in the presence of bacteria the drugs are released due to a change in the pH of the environment of any bacterial infected solution, solid, tissue or on any coating imaginable by a skilled person.

Advantageously, the material applied for synthesis of nanocontainers is magnetic, as it enables tracking of the magnetic nanocontainers by a magnetic field, and therefore of the sensor, equipped with these containers. Furthermore, the containers can be equipped with magnetic particles, to provide magnetic properties. The magnetic properties allow concentration of nanocontainers for medical treatment e.g. to guarantee efficient reduction of bacterial or germ infections. Besides various oxides, also carbodiimides, mixed compounds like $BaMF_4$ or $Pb_2MF_6$, $TbMnO_3$, $HoMnO_3$, $Ni_3V_2O_8$, can be applied, besides magnetic oxides, e.g. $Fe_3O_4$, $Cr_2O_3$, EuO, $CrO_2$.

The object of the present invention is further solved by a method for the manufacture of such a sensor comprising the following steps of
a) Providing a functional group-protected metastable scaffold
b) Linking the metastable scaffold with ligands,
c) Linking the metastable scaffold with a first linker-DNA and/or RNA
d) Coupling with the first linker-DNA and/or RNA to the scaffold
e) Coupling with a second linker-DNA and/or RNA to first linker-DNA and/or RNA
f) Deprotection of the functional groups of the scaffold.

The method according to this invention provides a metastable scaffold, functionalized with different groups to link further ligands, or ligands, binding sites or linkers or tethers to the scaffold. In a further embodiment of the present invention, the functionalized scaffold can be bound to any coating. Furthermore to a passive matrix or can be incorporated in various coatings, attached via its binding sites. The ligands can be at least partly matching, fully matching or mismatching DNA and/or RNA-sequences or fragments, containers, either filled or empty, or any other detecting system, useful in the sense of the present invention. A skilled person working knows certain techniques to insert the functional groups into such systems.

Figure 7:
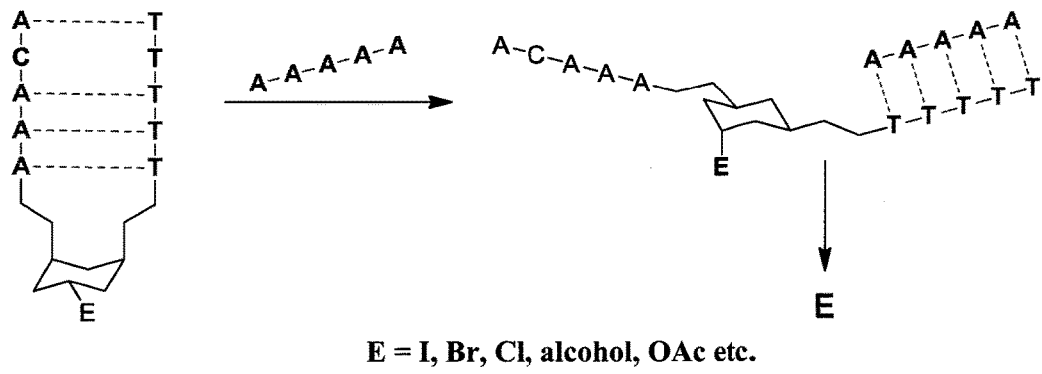

Furthermore the metastable scaffold can be coupled with linker-DNA and/or RNA, these sequences enable detection and tracking of bacterial DNA and/or RNA or other bacterial metabolism products or waste products, amino acids or peptides. FIG. 7 shows a metastable scaffold which is coupled with DNA on two sides of the cyclohexane-based scaffold. The two DNA strands coupled to the scaffold have at least partly complementary areas which hold the sensor in the metastable state in that the complementary DNA strands are attached to each other. In case any DNA-sequence wished to be detected comes in contact with the sensor it may bind to one of the DNA strands of the sensor thereby resulting in a conformational change of the cyclohexane ring.

The coupling with a second linker-DNA and/or RNA at least partly mismatching with the first linker-DNA and/or RNA forces the metastable scaffold in an energetically metastable conformational state via hybridization of the first and second DNA and/or RNA-strands (FIG. 7).

Finally, a deprotection step is proceeded to obtain a reactive scaffold with functional groups to bind it to coatings, further ligands, e.g. alcohols, esters, halides, sulfonates etc.

The method for manufacture of the sensor of the present invention is further generally demonstrated by the scheme in FIG. 8 and more detailed demonstrated in the following Scheme 1 which shows the general synthesis route of a bacterial sensor based on cyclohexane.

In a first step in Scheme 1 one hydroxyl group of cyclohexane-1,3,5-triol is protected by a first protecting group. A second hydroxyl group of the resulting compound (1) is than protected by a second protecting group. Compound (3) is produced in that 4-Bromobenzyl alcohol is coupled with Ethynyltrimethylsilane. The Trimethylsilane group of (3) is split from the compound and the hydroxyl group is substituted by a chlorine atom. The compound 5a is prepared using a similar protocol. In another reaction 2-Azidoacetic acid (6) is produced via the reaction of bromoacetic acid with sodium azide. Coupling of compound (6) with a oligonucleotide leads to compound (9) which then reacted with compound (8) resulting in compound (10). The first protecting group is then split off and the resulting alcohol is then reacted either with another compound (5) having an at least partly complementary DNA-strand and compound (9), or with compounds (5a) having an at least partly complementary DNA-strand (shown above) and (9). In a last step the second protecting group is split off resulting in a compound having two at least partly complementary DNA-strands.

Scheme 1:

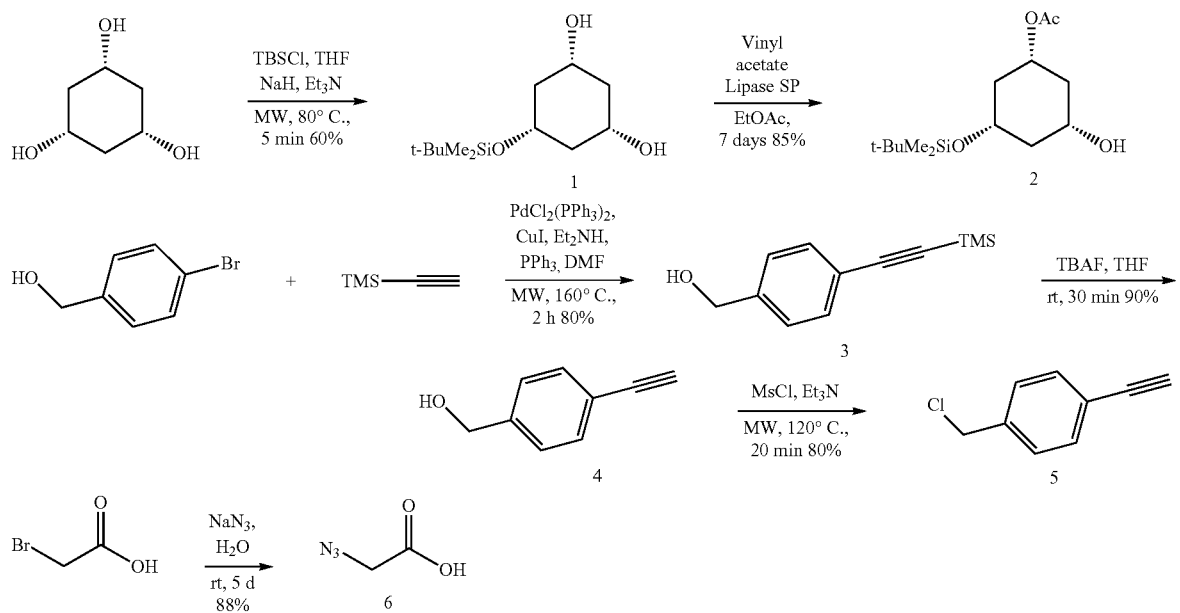

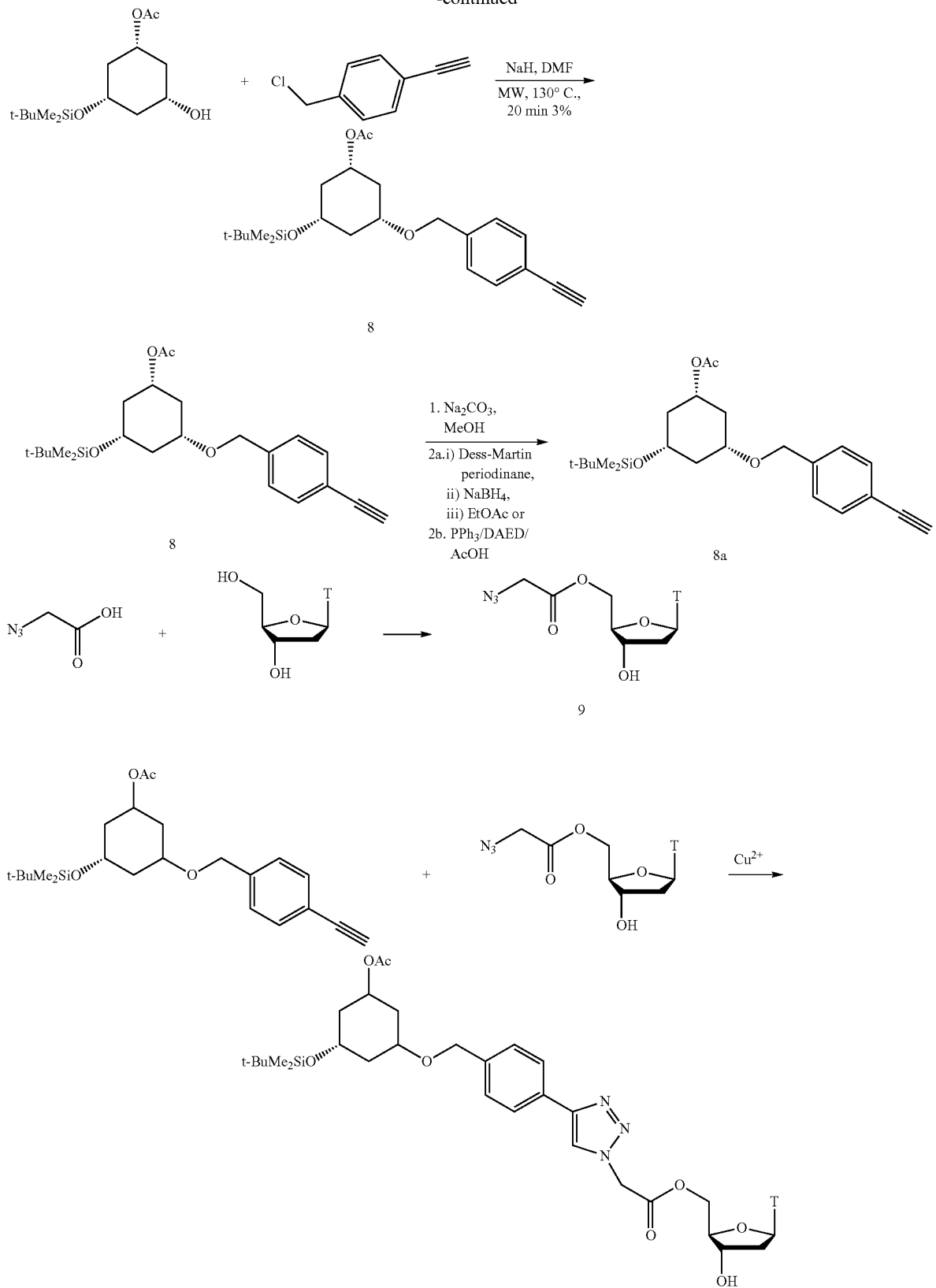

After obtention of 8, the all cis-stereoisomer can be inverted at the OAc-group by saponification (K$_2$CO$_3$/MeOH), followed by a Dess-Martin oxydation and subsequent reduction with NaBH$_4$ (or LiAlH(OMe)$_3$), and protection, leading to compound 8a. 8a can then be further functionalized as described. An alternative method is the inversion of the stereocenter of the cyclic alcohol by the Mitsunobu reaction.

The abbreviations in Scheme 1 have the following meanings: TBSCl means tert-Butyldimethylsilylchloride. TBAF means N-tetrabutylammonium fluoride. MsCl means methanesulfonyl chloride. MW means microwave. DMF means Dimethylformamide. THF means Tetrahydrofurane. TMS means Trimethylsilyl. T means in combination with the Desoxyribose and oligonucleotide.

Compound (5a) is shown in the following.

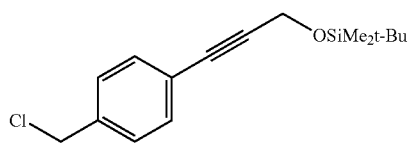

5a

Using 5a instead of 5, the reaction scheme 1 leads to compound 10a in analogy to compound 10 (scheme 2). This is an alternative route to the reaction shown in Scheme 1. Compound (10a) may then be reacted as done for compound (10) to obtain a compound having two complementary DNA-strands as explained in connection with scheme 1.

Scheme 2:

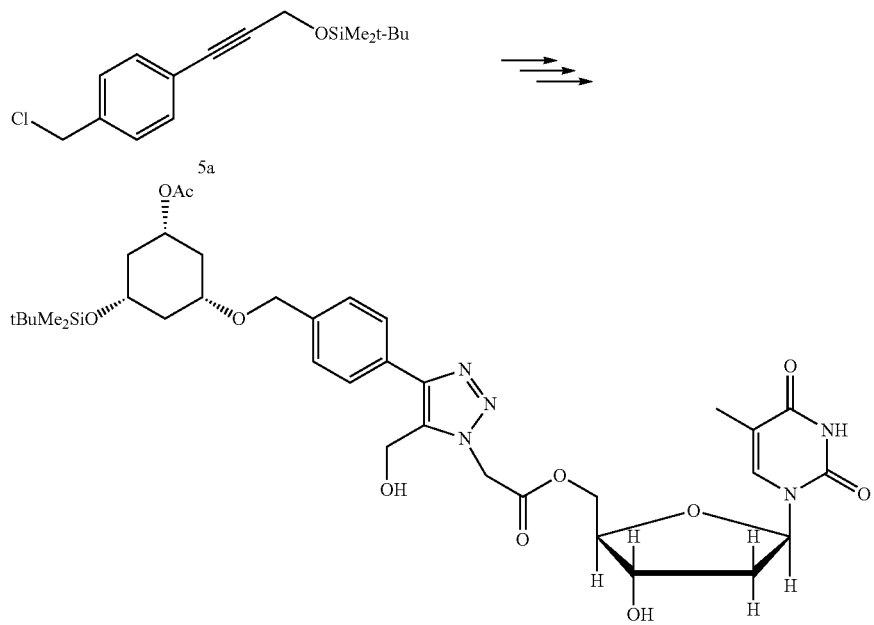

10a

The sensor according to the invention can be used for preventing infections of bacteria. With the invention of the sensor, bacterial infections can be detected and defeated in solutions, solids, tissue on implants, in and/or on coatings, of equipment, devices or any other application field imaginable where sterility is needed. As the sensor triggers drug release when bacteria are present a bacterial infection is effectively defeated, as the release is focused on the spot, where bacterial infections occur, without loss of drugs via dilution or the risk of breeding drug-resistant bacteria.

A further object of the present invention was to provide a method to prevent infections of bacteria with the antimicrobial system comprising the steps of
  a) Providing an antimicrobial system comprising a scaffold coupled with at least one drug-filled nanocapsule and linker-DNA and/or RNA
  b) Breaking the intramolecular pairing by coupling to a single-stranded DNA and/or RNA-strand of bacteria
  c) Triggering a conformational change of the scaffold by chemical reaction of the scaffold's ligands to stabilize the conformation
  d) Initiating a change in the pore size of the drug-filled nanocapsules
  e) Releasing drugs from the drug-filled nanocapsules.

The method to prevent bacterial infections provides an antimicrobial system, which is equipped with a scaffold which is coupled with at least one nanocapsule, filled with drugs, to defeat bacteria and a linker-DNA and/or RNA to detect bacteria in the environment. When bacteria are present the intramolecular pairing of the matching, mismatching or at least partly mismatching DNA and/or RNA-strands breaks which triggers the conformational change of the scaffold by a chemical reaction of the scaffolds ligands, to stabilize the new conformation.

The presence of bacteria provides bacterial DNA and/or RNA or at least bacterial metabolism or waste products, amino acids or peptides which can be detected by the pairing of the DNA and/or RNA-strands coupled to the scaffold. The DNA and/or RNA-pairing breaks, which releases the metastable, energetically unfavoured conformation of the metastable scaffold. The breakage of the DNA and/or RNA-pairing enables the conformational change, as the scaffold is not forced into the metastable conformation by the pairing of the DNA and/or RNA-strands. After the change different ligands can be in close proximity, which enables the chemical reaction of ligands, bound to the scaffold. This chemical reaction of the ligands leads further to a change of the pores of the drug-filled containers, preferably to an increase to enable the release of the encapsulated drugs via diffusion of the widening pores. As long as bacteria are present, the drugs are released, or new changes are initiated as long as drugs are needed to defeat the infection. After termination of the bacteria the drug release is stopped, to provide a secure inhibition of bacteria without the risk of breeding drug-resistant bacteria.

The use of an antimicrobial system prevents formation of biofilms. Coatings provided with attached or incorporated antimicrobial systems, which can be attached to any surface via linkers or tethers inhibit bacterial settlement and therefore the formation of drug-resistant biofilms. The antimicrobial system tracks bacteria before a biofilm formation can occur, or even in biofilms, triggering effective drugs to defeat the infection. To track bacteria with an antimicrobial system can even be affected by bacterial DNA and/or RNA, metabolism or waste products. Furthermore, after the formation of such biofilms, the antimicrobial system can be incorporate into these biofilms, triggering drug-release directly where bacteria are present.

A further object of the present invention is the use of an antimicrobial system for the detection of bacteria in solution. Only the presence of bacteria triggers drug release from the antimicrobial system equipped with drug-filled reservoirs. As it can directly be applied though the drugs are only released in the presence of bacteria and not lost by dilution, or decomposed by chemical influences of the solution such as temperature or any other harmful environmental factor.

Furthermore the antimicrobial system can be used to medicate bacterial infections in an effective and gentle way as less drugs are needed to defeat the bacterial infection than in other medications.

The present invention is further demonstrated by means of the following Examples which should, however, not understood as being limiting for the scope of the present invention:

EXAMPLES

General Methods:

Unless otherwise indicated, all reagents were obtained from commercial suppliers (Fluka, Aldrich, Arcos) and were used without further purification. Deuterated solvents were obtained from Cambridge Isotope Laboratories. Analytical thin layer chromatography was performed on Kieselgel F-254 pre-coated aluminum sheets TLC plates from Merck. Visualization was performed with a 254 nm UV lamp and/or a $KMnO_4$ solution. Flash column chromatography (FC) was carried out using Brunschwig silica gel (60 Å, 32-63 mesh). $^1$H NMR and $^{13}$C RMN spectra were recorded on a Bruker Avance DPX 360 spectrometer, a Fourier transform Bruker-DRX-300 spectrometer or a Bruker 400 spectrometer. All NMR spectra were recorded in $CDCl_3$, $CD_3CN$, DMSO-d6 (deuterated dimethylsulfoxide) or $D_2O$. Chemical shifts are expressed in parts per million (δ) using residual solvent protons as internal standards. Coupling constants (J) are reported in Hz. Splitting patterns are designated as s (singlet), d (doublet), dd (double doublet), t (triplet), dt (double triplet), q (quartet), bs (broad singlet), m (multiplet). A Perkin Elmer Lambda 40 UV/VIS spectrometer was employed for the electronic absorption spectra. Mass spectra at high resolution were recorded on a Bruker 4.7T BioApex II mass spectrometer. A Bruker Tensor 27 spectrometer was used to record IR spectra. LC-MS was performed on a Dionex Summit HPLC system, with an AQA ESI quadrupole detector.

Example 1

Synthesis of all-cis-5-((Tert-butyldimethylsilyl)oxy)cyclohexane-1,3-diol (1)

To a suspension of all-cis-cyclohexane-1,3,5-triol (100 mg, 0.757 mmol) (dried at 110° C. in high vacuum for 3 h to remove water of crystallization) in 2 ml of dry THF (Tetrahydrofurane) was added subsequently at room temperature TBS-Cl (tert-Butyldimethylsilylchloride) (125 mg, 0.832 mmol) and Triethylamine (0.086 ml, 0.616 mmol). One portion of NaH (36.3 mg, 0.832 mmol) was then added. The mixture was warmed up to 40° C. in 30 min and stirred at 40° C. for 2 h. The suspension was cooled to 8° C. and filtered. The filtrate was evaporated. The residue was triturated with 1 ml of hexane at room temperature and filtered. The filtrate was dried in high vacuum overnight to afford (1) (111 mg, 0.450 mmol, 59% yield) as a white solid.

Example 2

Synthesis of (1R,3S,5S)-3-((Tert-butyldimethylsilyl)oxy)-5-hydroxycyclohexyl acetate (2)

1 (3.660 g, 14.85 mmol) was dissolved in vinyl acetate (37.0 ml, 401 mmol) and 350 ml of ethyl acetate. Amano Lipase SP, from *burkholderia cepacia* (1 g, 0.00 µmol) was added and the mixture was stirred at room temperature for 10 days. The enzyme was filtered off, the filtrate concentrated and the residue dried overnight in high vacuum to afford 2 (2.356 g, 8.17 mmol, 55% yield) as a yellowish oil.

Example 3

Synthesis of (4-((Trimethylsilyl)ethynyl)phenyl)methanol (3)

A solution of 4-Bromobenzyl alcohol (1.276 g, 6.82 mmol), Ethynyltrimethylsilane (1.061 ml, 7.51 mmol), $PdCl_2(PPh_3)_2$ (24 mg, 0.034 mmol), Copper iodide (52 mg, 0.273 mmol), Triphenylphosphine (358 mg, 1.365 mmol), Diethylamine (10.70 ml, 102 mmol) in 2 ml of dry DMF (dimethylformamide) was heated under argon in a microwave oven at 150° C. for 30 min. The mixture was filtered. The filtrate was acidified with 1 M HCl and extracted 3 times with ether. The combined organic layers were washed with bicarbonate and water, dried over $MgSO_4$ and concentrated to afford 3 (1.274 g, 6.23 mmol, 91% yield) as a brown solid.

Example 4

Synthesis of (4-Ethynylphenyl)methanol (4)

3 (65 mg, 0.318 mmol) was dissolved in 1 ml of THF. TBAF (0.35 ml, 0.35 mmol) was added and the mixture was stirred at room temperature for 30 min. The solvent was removed under reduced pressure and the residue was purified by flash chromatography (AcOEt/Hexane 3:7) to afford 4 (37 mg, 0.28 mmol, 88% yield) as a colorless solid.

Example 5

Synthesis of 1-(Chloromethyl)-4-ethynylbenzene (5)

A solution of 4 (2.04 g, 15.44 mmol) in 1 ml of DCM (Dichlormethane) was cooled to 0° C. MsCl methanesulfonyl chloride (1.383 ml, 17.75 mmol) and Triethylamine (2.474 ml, 17.75 mmol) were added and the mixture was heated in a microwave oven at 100° C. for 20 min. The mixture was quenched with saturated NaHCO₃ (0.8 ml) and extracted with DCM. The organic layers were washed with water, dried over MgSO₄, filtered and concentrated under vacuum to afford 5 (2.004 g, 13.31 mmol, 86% yield) as a yellow oil.

Example 6

Synthesis of 2-Azidoacetic Acid (6)

NaN₃ (260 mg, 4 mmol) was dissolved in H₂O and bromoacetic acid (278 mg, 2 mmol) was added. After stirring the reaction mixture for 5 days at room temperature, concentrated HCl (0.3 ml) was added dropwise at 0° C. until pH=1. The aqueous layer was extracted 4 times with Et₂O, washed with brine and dried over MgSO₄. After removing the solvent under reduced pressure, 177 mg (1.751 mmol, 88%) of a colorless oil of 6 was recovered.

Example 7

Synthesis of the Oligonucleotides (7)

The oligonucleotides of the following sequences AAACA, TTTTT and AAAAA are synthesized with an automated synthesizer following a standard protocol.

Example 8

Synthesis of Compound (8) by Coupling of 2 with 5

For the synthesis of compound (8) as shown in Scheme 1 to a solution of 2 (42 mg, 0.146 mmol) in 0.2 ml of dry DMF at 0° C. was added NaH (7.62 mg, 0.175 mmol). The mixture was stirred for 10 min at 0° C. 7 (21.93 mg, 0.146 mmol) was added and the mixture was heated in a microwave oven at 100° C. for 1 h. The mixture was filtered, diluted with water and extracted with DCM. The organic layers were dried over MgSO₄ and concentrated. FC (flash chromatography) (Isolera EtOAc/Pentane 10%-->50% in 10 CV, 100% for 5 CV (column volume)) afforded 8 (2 mg, 0.005 mmol, 3.5% yield) as a yellow oil.

Example 8a

Conversion of Compound (8) into Compound (8a)

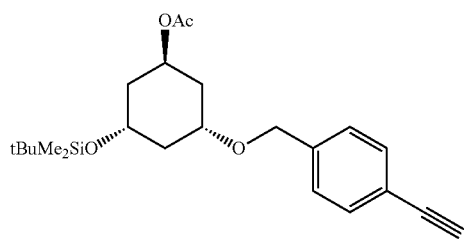

The stereoisomer 8a as shown above and in scheme 1 can be prepared from 8 by saponification of the acetate (K₂CO₃/MeOH), followed a) by oxidation (Dess-Martin), subsequent reduction with NaBH₄ (or LiAlH(OMe)₃) and reacetylation with acetic anhydride, or b) by a Mitsunobu reaction (Ph₃P, DAED, acetic acid) (DAED=diethylazodicarboxylate).

Example 9

Synthesis of Compound (9) by Coupling of 6 with 7

For the synthesis of compound (9) as shown in Scheme 1 above azidoacetic acid (8 mg, 0.080 mmol), DMAP (N,N-dimethylaminopyridine) (24 mg, 0.199 mmol) and the oligonucleotide (TTTTT) (123 mg, 0.08 mmol) are suspended in DMF (0.4 ml) at 0° C. EDC (15 mg, 0.08 mmol) is added. The reaction mixture is stirred at room temperature. The solvent is removed under reduced pressure.

Example 10

Synthesis of Compound (10) by Coupling of 8 with 9

For the synthesis of compound (10) as shown in Scheme 1 above copper(II) sulfate (0.555 mg, 3.48 µmol) and Sodium Ascorbate (0.689 mg, 3.48 µmol) were dissolved in 0.5 ml of water. The solution was added to a solution of 8a (1.4 mg, 3.48 µmol) and 9 (1.02 mg, 3.14 µmol) in 1 ml of MeCN. The mixture was heated in a microwave oven at 130° C. for 5 h, then was filtered and the filtrate was dried under vacuum. The product was observed by mass spectrometry.

Example 11

Deprotection of the Hydroxyl Group Protected with TBS of Compound (10)

To a mixture of 10 (1 mmol) in 10 ml of THF at 0° C. was added 2 ml of TBAF (N-tetrabutylammonium fluoride) 0.5 M in THF. The mixture was allowed to warm up to room temperature and was then stirred for 10 min. The mixture was then quenched with water and extracted with DCM. The collected organic layers were washed with brine and dried over MgSO₄, then concentrated under vacuum, thereby obtaining the deprotected compound (II).

Example 12

Coupling of 11 with 5 (12)

The hydroxyl group of compound (11) is then coupled with compound (5) in the same way as for the synthesis of compound (8) (see Example 8), thereby obtaining a compound (12).

Example 12a

Coupling of 11 with 5a (12a)

In the same way as in Example 12 compound (5a) is coupled with compound (11) resulting in compound (12a).

Example 13

Coupling of 12 with 9 (13)

Figure 8:
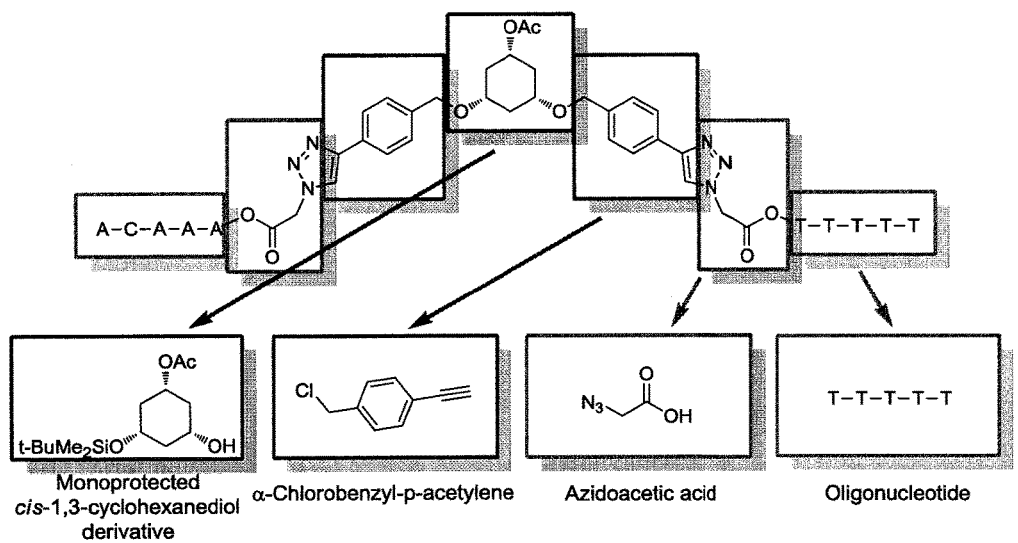

Compound (12) is coupled with compound (9) (wherein the Oligonucleotide is ACAAA) in the same way as for the synthesis of compound (10), thereby resulting in a sensor a shown in FIG. 8. After deprotection of the third alcohol group at the cyclohexyl-moiety of the compound shown in FIG. 8 by saponification with $Na_2CO_3$ and methanol a compound (13) as shown below is obtained:

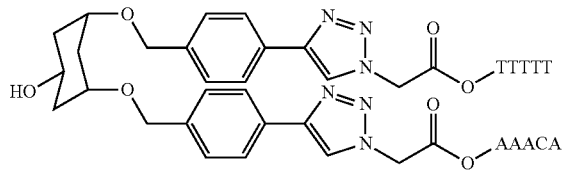

Example 13a

Coupling of 12a with 9 (13a)

Compound (12a) is coupled with compound (9) (wherein the Oligonucleotide is ACAAA) in the same way as for the synthesis of compound (10), thereby resulting in a sensor (13a) as shown below:

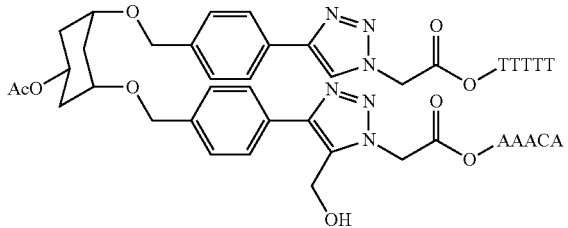

Example 14

Challenging the Sensor 12 mg of compound (13) or (13a) is dissolved in water (2 ml). Upon addition of 5 mg of the perfect match of AAAAA in water at 25° C., the conformational change is detected by $^1$H-NMR.

Example 15

Synthesis of $CeO_2$-Nanocontainers (Template Approach)

Cerium (III) acetylacetonate ($Ce(acac)_3$, Sigma-Aldrich), polyvinylpyrrolidone (PVP, average molecular weight 40,000, Sigma-Aldrich), potassium persulfate (KPS, Sigma-Aldrich), isonicotinic acid (Fluka), oxalyl chloride (Fluka), triethylamine (Acros Organics), ethylene glycol (Sigma-Aldrich), methylene chloride (Cambridge Isotope Laboratories), sodium bicarbonate ($NaHCO_3$, Sigma-Aldrich) silver (I) oxide (Acros Organics), sodium dodecyl sulfate salt (SDS, 85%, Sigma-Aldrich), urea (Sigma-Aldrich), silver nitrate (Carlo Erba Reagents), ethanol (Fluka), dichloromethane (Honeywell), toluene (Fluka) and ethyl acetate (Fluka) were of analytical grade and were used without further purification. Styrene (Fluka) and water were doubly distilled prior to use.

Synthesis of the Polystyrene Nanospheres Template

Anionic polystyrene nanospheres were synthesized via emulsion polymerization according to the method from Kartsonakis et al (Kartsonakis, I. A.; Liatsi, P.; Daniilidis, I.; Kordas, G.; J. Am. Ceram. Soc., 91 (2), 372-378). The reaction mixture was prepared by mixing 3.70 g of styrene, 0.30 g KPS, 0.09 g SDS in 250 mL of water. The solution was stirred at 80° C. under argon for 42 hours. The polystyrene nanospheres were washed three times by centrifuging the solution for 30 min at 10 000 rpm, discarding the supernatant and resuspending the pellets in water.

Synthesis of $CeO_2$ Nanocapsules

The coating procedure via a sol-gel method was obtained from Kartsonakis et al as mentioned above. 0.280 g of the obtained polystyrene nanospheres, 0.670 g $Ce(acac)_3$, 0.400 g PVP, 0.250 g urea and 40 mL water were mixed for few minutes. Then the reagents were allowed to react at 100° C. for 4 to 5 days without any agitation. The suspension was centrifuged for 30 min at 10 000 rpm. The supernatant was discarded and the pellets were resuspended in water using sonication. This washing step was repeated 3 times and the core/shell particles were dried in an oven at 40° C. for at least one day. The polystyrene core was removed by calcination in an oven exposed to air at a temperature of 600° C. for five hours, resulting in empty ceria nanocapsules.

Example 16

Synthesis of a Compound Ag(L)$NO_3$ and its Encapsulation into $CeO_2$ Nanocapsules Step a: Synthesis of ligand (L)
Ethane-1,2-dioxy-1,2-di-isonicotinate The ligand was synthesized under argon atmosphere by dissolving 10 g of isonicotinic acid in 200 mL toluene and adding dropwise 5.2 mL of oxalyl chloride. The mixture was stirred overnight at room temperature. After the addition of 45.3 mL of triethylamine, the mixture was refluxed for 30 minutes. Then the solution was allowed to cool down and 1.8 mL of ethylene glycol was added dropwise. The solution was brought back to reflux and stirred for two days. The ligand was filtered off the reaction mixture and, after the addition of methylene chloride, was washed once with a NaHCO$_3$ saturated solution and twice with water. After being filtered off, the ligand was recrystallized twice in ethyl acetate.

Step b: Encapsulation of Ag(L)NO$_3$ in CeO$_2$ Nanocapsules

The method used to encapsulate silver nitrate and its ligand inside the ceria nanocapsules was inspired from Kartsonakis et al (Kartsonakis, I.; Daniilidis, I.; Kordas, G.; J. Sol-Gel Sci. Technol. 2008, 48, 24-31). The complex was encapsulated in two steps: 1) first the encapsulation of AgNO$_3$, followed by 2) the encapsulation of the ligand. In each step, the nanocapsules were submitted to vacuum. Then the capsules were immersed in saturated solutions of 1) silver nitrate in ethanol, and 2) ligand in dichloromethane. The mixture was stirred for 2 hours at room temperature. After three washings in the respective solvent, the capsules were dried overnight in an oven at 40° C.

Example 17

Synthesis of SiO$_2$-Nanocontainers (Microemulsion Approach)

Chemicals:
  Microemulsion
    cyclohexane (oil phase)
    doubly deionized water (water phase)
    TritonX-100=polyoxyethylene octyl phenyl ether (non-ionic surfactant)
    n-hexanol (co-surfactant)
  Silica precursors
    TEOS=tetraethyl orthosilicate
    APTS=(3-aminopropyl) trimethoxysilane
  Basic catalyst—ammonia (28-30 wt %)
  Washing
    EtOH
    MiliQ water 8 mL (0.064 mol) of n-hexanol and 1.8 mL (0.1 mol) of doubly deionized water and 10 g of TritonX-100 are added to 29.65 g (0.352 mol) of cyclohexane (under nitrogen) and it is stirred for 5 days under nitrogen. Then 100 μL (0.5 mmol) of TEOS are added and it is stirred for 2 hours. After 2 hours, 250 μL of ammonia is added and after 2 hours 50 μL of solution of 0.1 mL (0.6 mmol) APTS in 1.5 mL (0.257 mol) EtOH are added. It is stirred for 24 h. After 24 h the reaction mixture is centrifuged (10,000 rpm, 30 min, rt) and the precipitate is washed twice with 25 mL of EtOH and centrifuged again (10,000, min, rt). The precipitate is resuspended in MiliQ water and stirred for a certain time (see Table 1). Depending on the time and the temperature, the interior of the silica spheres can be removed to different degree (see Table 1). After washing, samples are centrifuged (10,000, 15 min, rt) again and the precipitate is transferred to fresh MiliQ water, where it remains stable for more than 1 week.

TABLE 1

Influence of washing condition on the removal of core from silica nanospheres.

Figure 9:
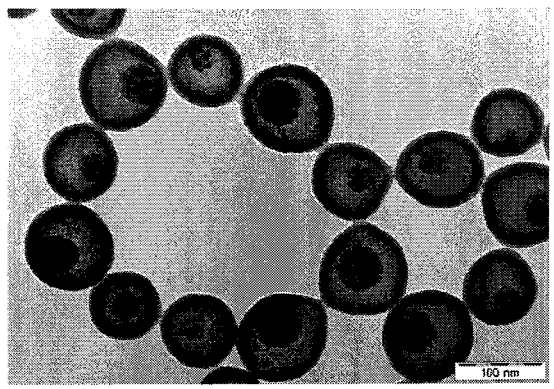
Figure 10:
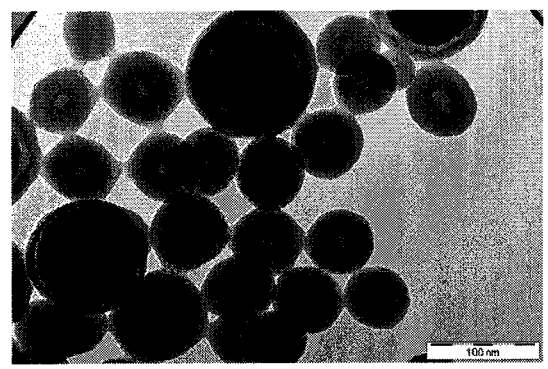
Figure 11:
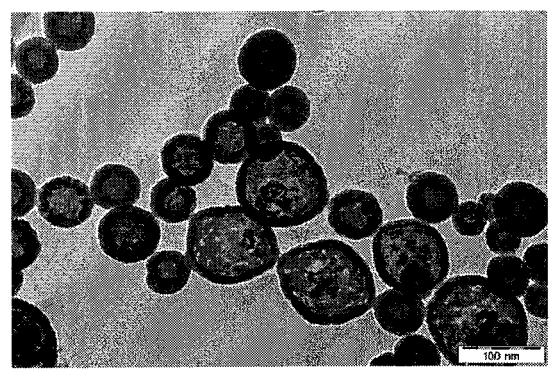

| Temperature: 40° C. | Temperature: 40° C. | Temperature: 70-80° C. |
|---|---|---|
| Time: 40 minutes | Time: 2 hours | Time: 2 hours |
| FIG. 9 | FIG. 10 | FIG. 11 |

FIGS. 9 to 11 show the resulting silica nanospheres in dependence from the temperature and the time of washing. It can be seen from FIG. 11 that the interior of the silica spheres can be mostly removed.

Example 18

Incorporation of AgL(NO$_3$) into the SiO$_2$-Nanocontainers

Figure 12:
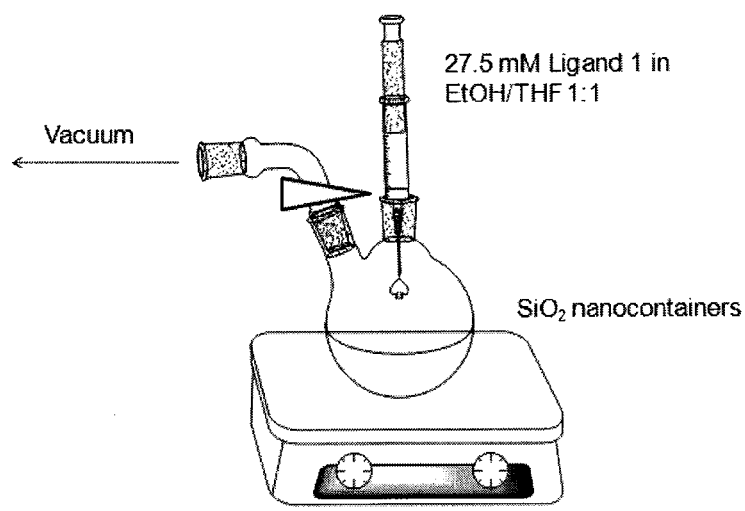

Incorporation of drug (ligand 1) into nanocontainers of SiO$_2$ occurs in analogy to the method described for AgL (NO$_3$) into CeO$_2$-capsules via a set for the incorporation of drugs into silica nanocontainers shown in FIG. 12.

Example 19

Attaching the Nanocontainers to the Sensor

CeO$_2$— or SiO$_2$-nanocontainers, filled with Ag-compound, are placed in a basic bath of NaOH 0.1 M for 3 h at 80° C. The containers are washed with water and dried under vacuum. The IR-spectra of the samples show the presence of functional OH-groups at the surface of the nanocontainers. The capsules are then treated directly with an excess of di-acid chloride of the type ClOC—(CH$_2$CH$_2$O)$_n$—COCl (linker) in order to obtain the acid chloride coated surface. Extreme care has to be taken during this reaction in order to avoid humidity. The dried samples are suspended in dry THF and the sensor is added: The nanocontainers with acid chloride functionality (20 mg) are suspended in anhydrous tetrahydrofuran (2 ml) and the sensor, derived from 10a (12 mg), is added in THF (1 ml), and the mixture is stirred for 24 hours at room temperature. The mixture is then filtered and washed with two portions of cold, anhydrous THF. IR-spectra of the nanocontainer show now the presence of organic material attached to them.

Example 20

Figure 13:
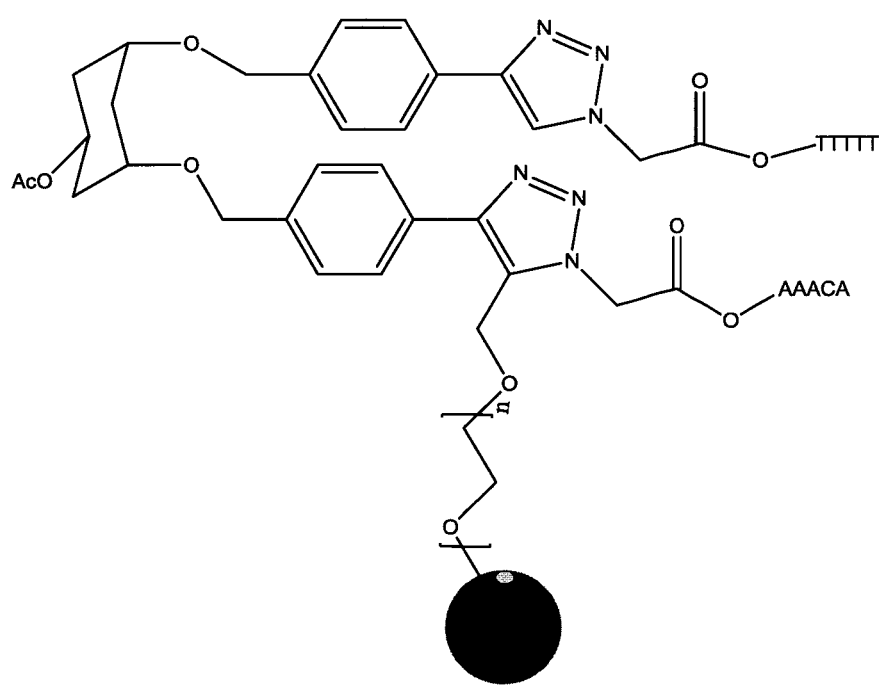

Coupling of Compound (13a) to the Linker on the Surface of the CeO$_2$— or SiO$_2$-Nanocontainer Filled with Ag-Compound Compound (13a) is linked to the nanocontainer by standard methods via reaction of the free —OH group of compound (13a) with the acid-chloride of the linker resulting in an ester as shown in FIG. 13. The sphere in FIG. 13 depicts the nanocontainer.

Example 21

Testing of the Coupled Compound Obtained in Example 20

The compound obtained in Example 20 is tested in the following way: To an aqueous solution containing the compound and iodide-ions the oligonucleotide AAAAA is given resulting in the occurrence of a yellowish precipitate of Ag-iodide. This proves the functioning of the bacterial sensor in the presence of silver-filled nanocontainers.

Example 22

Coupling of Compound (13) with Vancomycin

Vancomycin (Van) has the following structure (the C-terminal of Van may be verified/modified/functionalized without altering its activity):

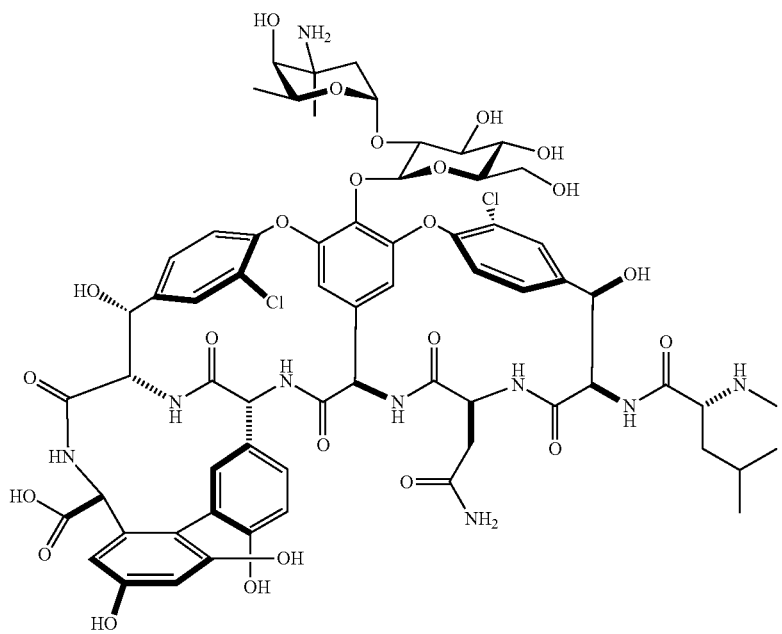

Figure 14:
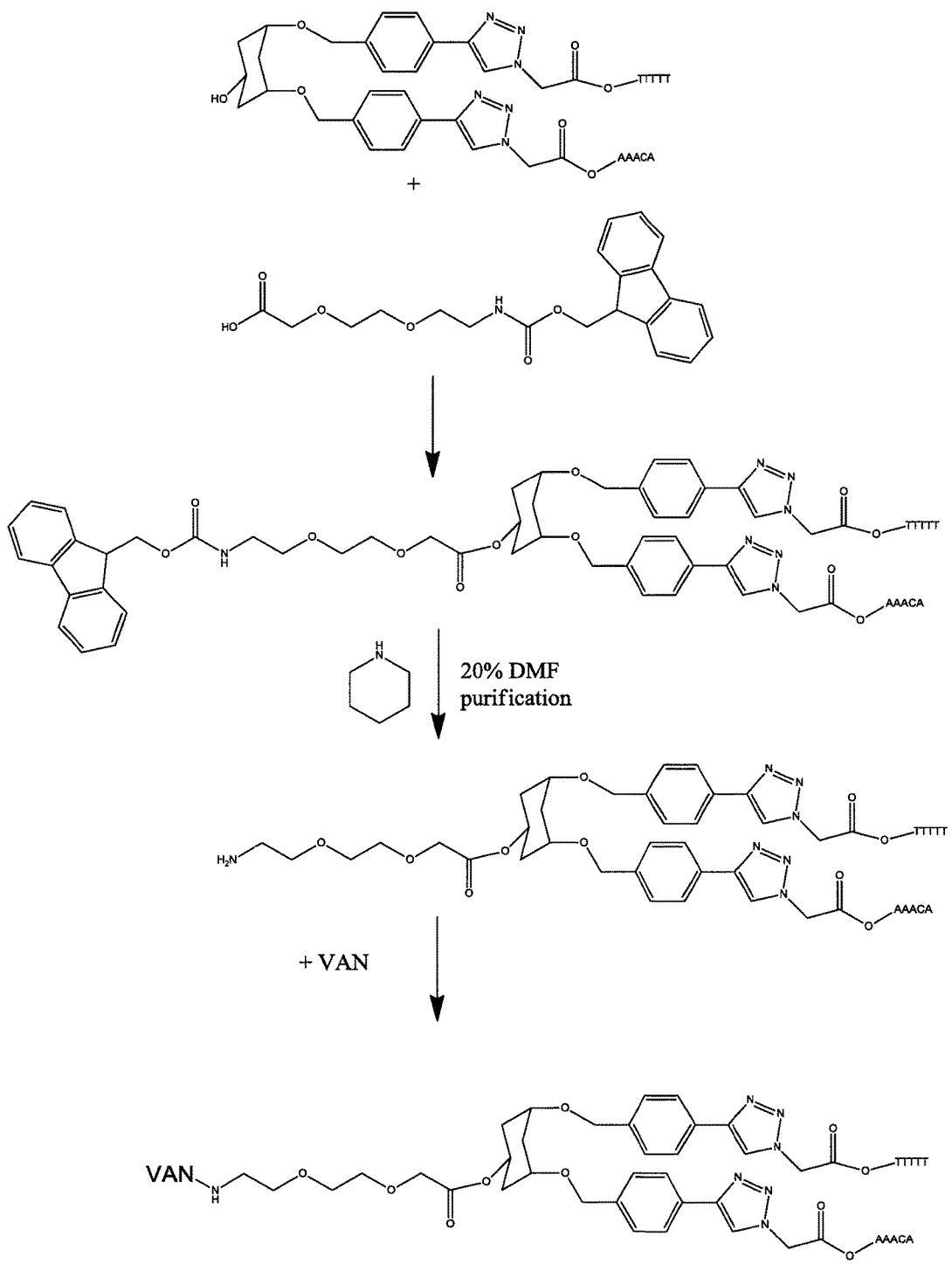

Compound (13) is the coupled to the Fmoc-8-amino-3,6-dioxaoctanoic acid (AEEA) linker via the following procedure:

In an esterification reaction between compound (13) and Fmoc-8-amino-3,6-dioxaoctanoic acid by a) dissolving triethylamine and DMAP (dimethylaminopyridine) (10 mol %) with 2-methyl-6-nitrobenzoic anhydride, b) addition of the acid, followed by addition of compound 13. After stirring at room temperature for 6 h, the ester is obtained in 83% yield. To the solution of 10 mg of the ester compound (AEEA-13) in 2 mL of dimethyl formamide (DMF) were added 0.3 g of vancomycin. The mixture was cooled to 0° C., and 110 mg of HATU (2-(1H-7-Azabenzotriazol-1-yl)-1,1,3,3-tetramethyl uronium hexafluorophosphate Methanaminium) was added, followed by 0.2 mL of diisopropylethylamine (DIEA). The solution was stirred 1 h at 0° C. and then allowed to warm to room temperature and stirred overnight. Removal of the solvent afforded the crude product. This crude product was dissolved in water and $CH_2Cl_2$ and the aqueous phase was extracted. This crude product was purified by preparative reverse-phase HPLC (linear gradient from 5% to 40% using 0.1% TFA in acetonitrile for 30 min) and lyophilized to afford 7.5 mg of VAN-AEEA-13. The reaction for obtaining this compound is shown in FIG. 14.

Example 23

Testing of Compound VAN-AEEA-13

6 mg of compound VAN-AEEA-13 is dissolved in water. To this solution 1 eq of the Oligonucleotide AAAAA is added. Analytical methods show that the reaction of reductive elimination of VAN-AEEA occurs due to the addition of AAAAA, thereby proving that the change of conformation of the cyclohexane-moiety results in the elimination of compound VAN-AEEA.

The invention claimed is:

1. A sensor for sensing a trigger, the sensor comprising:
an intrinsically metastable scaffold, wherein the scaffold has a plurality of changeable conformations, and wherein the scaffold comprises
locking-ligands
and a drug-filled container,
wherein the locking-ligands are matching, mismatching or partly mismatching DNA and/or RNA-strands and wherein pairing of the locking-ligands keeps the scaffold in an intrinsically metastable position in the absence of the trigger, while a break of an interaction between the locking-ligands induces a change in the conformation of the scaffold in the presence of the trigger;
wherein the scaffold has at least one ligand and
wherein at least one ligand comprises a container and wherein the conformational change of the scaffold initiates an intramolecular chemical reaction of the at least one ligand, the intramolecular chemical reaction triggering compounds release from the container.

2. The sensor according to claim 1, wherein the at least one ligand is selected from reactive or non- reactive ligands, DNA- and/or RNA-strands, sugars, peptides, amino acids, enzyme-substrate-complexes, or enzymes or substrates, organometallic and coordination compounds, compound-filled containers, functionalized ligands, alcohols and indicators.

3. The sensor according to claim 1, wherein the trigger for the scaffold's conformational change is selected from the group of the presence of bacteria, a virus, germs, moulds, fungus, metabolic or waste products, metabolic or waste product of any microbe or bacteria, peptides, amino acids, toxins, toxic substances, microbes, spores, disease- genes, and an environmental change, change in temperature, pH, ion concentration, magnetic influences, pressure, osmosis, or concentration gradients.

4. The sensor according to claim 1, wherein the trigger is the presence of a bacterium.

5. The sensor according to claim 1 wherein the compounds are selected from a group of drugs, antibiotics, metal salts, sulfates, sulfazines, sulfadiazines, indicators, denaturating agents, metalorganic complexes, buffers, alcohols, magnetic compounds, and vesicles.

6. The sensor according to claim 1, wherein the container is a porous nanocapsule filled with compounds.

7. The sensor according to claim 6, wherein a pore size of the nanocapsule is reversibly changeable.

8. The sensor according to claim 7, wherein the change in the pore size is induced by environmental factors.

* * * * *